(12) United States Patent
Shioji et al.

(10) Patent No.: US 8,420,865 B2
(45) Date of Patent: Apr. 16, 2013

(54) PHOSPHINE COMPOUND, PROCESS FOR PRODUCING THE SAME, AND PEROXIDE SCAVENGER USING THE SAME

(75) Inventors: Kosei Shioji, Fukuoka (JP); Hiroyuki Nakagawa, Fukuoka (JP); Kentaro Okuma, Fukuoka (JP)

(73) Assignee: Fukuoka University, Fukuoka-shi (JP)

( * ) Notice: Subject to any disclaimer, the term of this patent is extended or adjusted under 35 U.S.C. 154(b) by 181 days.

(21) Appl. No.: 12/921,967

(22) PCT Filed: Mar. 10, 2009

(86) PCT No.: PCT/JP2009/054551
§ 371 (c)(1),
(2), (4) Date: Sep. 10, 2010

(87) PCT Pub. No.: WO2009/113543
PCT Pub. Date: Sep. 17, 2009

(65) Prior Publication Data
US 2011/0015440 A1    Jan. 20, 2011

(30) Foreign Application Priority Data

Mar. 11, 2008   (JP) .................... 2008-060715

(51) Int. Cl.
C07F 9/54       (2006.01)
(52) U.S. Cl.
USPC ..................... 568/10; 568/8; 568/9
(58) Field of Classification Search .......... 568/10, 568/8, 9; 558/32
See application file for complete search history.

(56) References Cited

U.S. PATENT DOCUMENTS

| | | | | |
|---|---|---|---|---|
| 5,202,493 A | * | 4/1993 | Burk | 568/12 |
| 5,824,822 A | * | 10/1998 | Saito et al. | 568/10 |
| 6,774,265 B2 | * | 8/2004 | Yaowu | 568/10 |
| 2003/0144138 A1 | * | 7/2003 | Matsumura et al. | 502/162 |
| 2003/0216599 A1 | * | 11/2003 | Hillhouse | 568/10 |
| 2003/0236433 A1 | * | 12/2003 | Hoge et al. | 562/553 |
| 2005/0098765 A1 | * | 5/2005 | Rooney | 252/600 |

OTHER PUBLICATIONS

"Oxidative Stress", Japanese Society of Antioxidants, http://www.jsa-site.com/sanka_storesu.htm.
Ban et al., "Novel mitochondria-localizing TEMPO derivative for measurement of cellular oxidative stress in mitochondria", Bioorganic & Medicinal Chemistry Letters, 2007, 17, pp. 2055-2058.
International Search Report—dated Apr. 14, 2009 for PCT/JP2009/054551.
Okimoto et al., "A novel fluorescent probe diphenyl-1 pyrenylphosphine to follow lipid peroxidation in cell membranes", FEBS Letters, 2000, 474, pp. 137-140.

* cited by examiner

*Primary Examiner* — Johann Richter
*Assistant Examiner* — Pancham Bakshi
(74) *Attorney, Agent, or Firm* — Birch, Stewart, Kolasch & Birch, LLP.

(57) ABSTRACT

The invention provides a novel peroxide scavenger comprising a phosphine compound represented by general formula [I]:

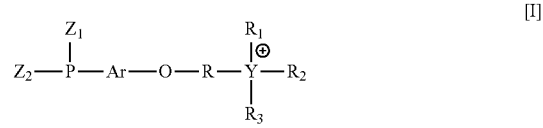

wherein $Z_1$ and $Z_2$ each represents a cyclic group; Ar represents an arylene group; R represents an aliphatic hydrocarbon group; Y represents phosphorus (P), nitrogen (N), or bismuth (Bi); and $R_1$, $R_2$, and $R_3$ each represents a cyclic group, particularly a peroxide scavenger that can scavenge peroxides such as reactive oxygen species which are generated in mitochondria upon exposure to oxidative stress and localized in mitochondria. The phosphine compound of the invention is oxidized by the peroxides localized in mitochondria to increase the fluorescence intensity, whereby the peroxides can be scavenged.

11 Claims, 5 Drawing Sheets a) Mito Tracker Green FM b) MitoDPPPO

Microscopic observation of MitoDPPPO loading into HepG2 cells
a) Staining with Mito Tracker Green FM   b) Staining with MitoDPPPO ◆ : No additive
■ : Ascorbic acid
▲ : 6-O-Acetylascorbic acid
× : 6-O-Hexanoylascorbic acid
＊ : 5, 6-O-Isopropylidene-L-ascorbic acid ◆ : No additive
■ : Ascorbic acid
▲ : 6-O-Acetylascorbic acid
×: 6-O-Hexanoylascorbic acid
✻: 5, 6-O-Isopropylidene-L-ascorbic acid

PHOSPHINE COMPOUND, PROCESS FOR PRODUCING THE SAME, AND PEROXIDE SCAVENGER USING THE SAME

TECHNICAL FIELD

This invention relates to phosphine compounds and peroxide scavengers using the same. More particularly, this invention relates to phosphine compounds and scavengers using the same, which are peroxide scavengers localized in mitochondria. This invention also relates to novel phosphine compounds localized in mitochondria and a process for producing the same as well as a method for scavenging peroxides. This invention further relates to phosphinyl compounds which are the oxidation products of the phosphine compounds.

BACKGROUND ART

Oxidative stress is defined as an imbalance between the oxidative damages of reactive oxygen species produced in vivo and the antioxidant potential of biological antioxidative system. Originally, reactive oxygen species are useful products which are formed during energy generation, xenobiotic attack, disposal of unnecessary cells, cellular signaling, etc. Once excessive reactive oxygen species unable to be scavenged by the biological antioxidative system are generated, however, these species oxidize the lipids, proteins or enzymes that serve the structures or functions in living organisms or genetic DNA carrying genetic information, cause damages, disrupt the structures or functions in living organisms, cause diseases such as cancer or lifestyle-related disease, or accelerate the aging process (Non-Patent Document 1).

Peroxides such as active oxygen produced in vivo when $H_2O$ is formed from the oxygen taken up during respiration in the mitochondrial electron transport system are thought to increase oxidative stress. It is known that mitochondria not only make up ATP to sustain cell life but also play a crucial role in aboptosis (cell death). Oxidized LDL, oxidized RLP, etc. are also known to increase oxidative stress in vascular endothelial cells.

As such, mitochondria are the source for generating reactive oxygen and on the other hand, mitochondria are one of organelles which are most vulnerable to oxidative stress. Therefore, analysis of oxidative stress in mitochondria is greatly helpful to elucidate the mechanisms of many diseases associated with oxidative stress. For this reason, it is extremely useful to produce functional molecules for visualizing the level of oxidative stress in mitochondria.

Peroxide scavengers have been developed so far but no reagent for exclusively scavenging peroxides alone has been developed (Non-Patent Document 2). No peroxide scavenger localized in mitochondria has been developed, either (Non-Patent Document 3).

[Non-Patent Document 1] Web site of Japanese Society of Antioxidants (http://www.jsa-site.com/sanka_storesu.htm)
[Non-Patent Document 2] Suzuki, B., et al., Bioorg. Med. Chem. Lett. 2007, 2055-2058
[Non-Patent Document 3] Okimoto, Y., et al., FEBS Lett., 2000, 474, 137-140

DISCLOSURE OF INVENTION

In view of the background art as described above, the present inventors have found a novel peroxide scavenger where a diphenylmonopyrenyl phosphine compound which is a substituent localized in mitochondria is loaded as a fluorescence probe for scavenging peroxides only. This invention has thus been accomplished.

In one aspect, an object of this invention is to provide a phosphine compound represented by general formula [I] below and a process for producing the same.

In another aspect, an object of this invention is to provide a novel peroxide scavenger wherein the peroxide scavenger is the phosphine compound [I], and a method for using the same.

In a further aspect, an object of this invention is to provide a phosphinyl compound represented by general formula [I'] below, which is produced through oxidation of the novel peroxide scavenger, i.e., the phosphine compound.

In order to achieve the foregoing objects, this invention provides the phosphine compound represented by general formula [I] below:

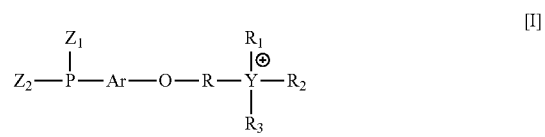

wherein:
$Z_1$ and $Z_2$ each represents a cyclic group;
Ar represents an arylene group;
R represents an aliphatic hydrocarbon group;
Y represents phosphorus (P), nitrogen (N) or bismuth (Bi); and,
$R_1$, $R_2$ and $R_3$ each represents a cyclic group.

In a preferable embodiment, this invention provides the phosphine compound described above, wherein:
the cyclic groups shown by each of $Z_1$ and $Z_2$ both are unsubstituted or substituted monocyclic hydrocarbon groups or polycyclic hydrocarbon groups or hetero-monocyclic groups or hetero-polycyclic groups;
the arylene group shown by Ar is an unsubstituted or substituted monocyclic hydrocarbon group or bicyclic hydrocarbon group;
the aliphatic hydrocarbon group shown by R is a linear or branched bivalent aliphatic hydrocarbon group having 1 to 8 carbon atoms;
the cyclic groups shown by $R_1$, $R_2$ and $R_3$, which may be the same or different, each independently represents an unsubstituted or substituted monocyclic hydrocarbon group or polycyclic hydrocarbon group or hetero-monocyclic group or hetero-polycyclic group;
with the proviso that either one of the cyclic groups represented by $Z_1$ and $Z_2$ is a monocyclic hydrocarbon group or a hetero-monocyclic group and the other cyclic group is a polycyclic hydrocarbon group or a hetero-polycyclic group, and/or either one of the cyclic groups represented by $R_1$, $R_2$ and $R_3$ is a monocyclic hydrocarbon group or a hetero-monocyclic group, and the other cyclic group(s) is/are a polycyclic hydrocarbon group(s) or a hetero-polycyclic group(s).

In a more preferable embodiment of this invention, the invention provides the phosphine compound represented by general formula [I] described above, in which either one of the cyclic groups represented by $Z_1$ and $Z_2$ is a polycyclic hydrocarbon group or a hetero-polycyclic group, the other monocyclic group is a monocyclic hydrocarbon group or a hetero-monocyclic group, all of the cyclic groups represented by $R_1$, $R_2$ and $R_3$ are monocyclic hydrocarbon groups or hetero-monocyclic groups, or, the monocyclic groups in all of the cyclic groups represented by $Z_1$ and $Z_2$ are monocyclic hydrocarbon groups or hetero-monocyclic groups, either one of the cyclic groups represented by $R_1$, $R_2$ and $R_3$ is a polycyclic hydrocarbon group or a hetero-polycyclic group, and the other cyclic group(s) is/are a monocyclic hydrocarbon group(s) or a hetero-monocyclic group(s).

In a more preferable embodiment, this invention provides the phosphine compound represented by general formula [I] described above wherein:

in the cyclic groups represented by $Z_1$ and $Z_2$, the monocyclic hydrocarbon group is, e.g., phenyl; the polycyclic hydrocarbon group includes a bicyclic hydrocarbon group, e.g., indanyl, indenyl, pentalenyl, azulenyl, naphthyl, tetrahydronaphthyl, etc.; a tricyclic hydrocarbon group, e.g., anthracenyl, fluorenyl, phenalenyl, phenanthrenyl, etc.; a tetracyclic hydrocarbon group, e.g., pyrenyl, naphthacenyl, chrysenyl, etc.; a pentacyclic hydrocarbon group, e.g., perylenyl, picenyl, pentacenyl, etc.; a hexacyclic hydrocarbon group, e.g., naphthobyrenyl, etc.; or a heptacyclic hydrocarbon group, e.g., coronenyl, etc.; in the heterocyclic group, the hetero-monocyclic group includes a N-containing hetero-monocyclic group, e.g., pyrrolyl, imidazolyl, pyrazolyl, pyridyl, piperidyl, triazinyl, etc.; an O-containing hetero-monocyclic group, e.g., furanyl, pyranyl, etc.; a S-containing hetero-polycyclic group, e.g., thiophenyl, etc.; and a N/O/S-containing hetero-monocyclic group, e.g., oxazolyl, thiazolyl, morpholinyl, etc.; the hetero-polycyclic group includes a N-containing hetero-polycyclic group such as a N-containing hetero-bicyclic group, e.g., indolyl, indolinyl, quinolinyl, isoquinolinyl, quinazolinyl, quinoxalinyl, naphthyridinyl, puteridinyl, purinyl, etc.; and a N-containing hetero-tricyclic group, e.g., acridinyl, carbazolyl, phenanthridinyl, phenazinyl, benzoisoquinolinyl, etc.; an O-containing hetero-polycyclic group such as an O-containing hetero-bicyclic group, e.g., benzofuranyl, chromanyl, chromenyl, isochromanyl, etc., and an O-containing hetero-tricyclic group, e.g., xanthenyl, etc.; a S-containing hetero-polycyclic group such as a S-containing hetero-tricyclic group, e.g., dithianaphthyl, etc., a S-containing hetero-tricyclic group, e.g., thianthrenyl, etc.; and a N/O/S-containing hetero-polycyclic group, e.g., pyridoxazolyl, thienofuranyl, phenoxazinyl, phenothiazinyl, pyrazoloxazolyl, etc.; wherein the substituent includes a lower aliphatic hydrocarbon group having 1 to 6 carbon atoms, e.g., methyl, ethyl, propyl, isopropyl, etc.;

the arylene group shown by Ar is phenylene, tolylene or naphthalene;

the linear or branched bivalent aliphatic hydrocarbon group having 1 to 8 carbon atoms, which is shown by R, is methylene, ethylene, propylene, isopropylene, butylene or isobutylene; and, in the cyclic groups represented by $R_1$, $R_2$ and $R_3$ of the cationic group shown by A, the monocyclic hydrocarbon group is, e.g., phenyl, etc.; the polycyclic hydrocarbon group includes a bicyclic hydrocarbon group, e.g., indanyl, indenyl, pentalenyl, azulenyl, naphthyl, tetrahydronaphthyl, etc.; a tricyclic hydrocarbon group, e.g., anthracenyl, fluorenyl, phenalenyl, phenanthrenyl, etc.; a tetracyclic hydrocarbon group, e.g., pyrenyl, naphthacenyl, chrysenyl, etc.; a pentacyclic hydrocarbon group, e.g., perylenyl, picenyl, pentacenyl, etc.; a hexacyclic hydrocarbon group, e.g., naphthobyrenyl, etc.; or a heptacyclic hydrocarbon group, e.g., coronenyl, etc.; in the heterocyclic group, the hetero-monocyclic group includes a N-containing hetero-monocyclic group, e.g., pyrrolyl, imidazolyl, pyrazolyl, pyridyl, piperidyl, triazinyl, etc.; an O-containing hetero-monocyclic group, e.g., furanyl, pyranyl, etc.; a S-containing hetero-polycyclic group, e.g., thiophenyl, etc.; and a N/O/S-containing hetero-monocyclic group, e.g., oxazolyl, thiazolyl, morpholinyl, etc.; the hetero-polycyclic group includes a N-containing hetero-polycyclic group such as a N-containing hetero-bicyclic group, e.g., indolyl, indolinyl, quinolinyl, isoquinolinyl, quinazolinyl, quinoxalinyl, naphthyridinyl, puteridinyl, purinyl, etc.; and a N-containing hetero-tricyclic group, e.g., acridinyl, carbazolyl, phenanthridinyl, phenazinyl, benzoisoquinolinyl, etc.; an O-containing hetero-polycyclic group such as an O-containing hetero-bicyclic group, e.g., benzofuranyl, chromanyl, chromenyl, isochromanyl, etc., and an O-containing hetero-tricyclic group, e.g., xanthenyl, etc.; a S-containing hetero-polycyclic group such as a S-containing hetero-tricyclic group, e.g., dithianaphthyl, etc., a S-containing hetero-tricyclic group, e.g., thianthrenyl, etc.; and a N/O/S-containing hetero-polycyclic group, e.g., pyridoxazolyl, thienofuranyl, phenoxazinyl, phenothiazinyl, pyrazoloxazolyl, etc.; wherein the substituent includes a lower aliphatic hydrocarbon group having 1 to 6 carbon atoms, e.g., methyl, ethyl, propyl, isopropyl, etc.

Since the phosphine compound represented by general formula [I] described above is in a cationic state, the compound is preferably in such a configuration that binds to an anion, as shown by general formula [II] below. The cation includes halogen ions such as chlorine, bromine, or iodine, etc. Consequently, these anion-bound compounds are also included as one embodiment of this invention:

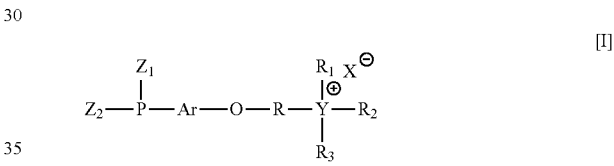

(wherein X means a halogen atom).

In another aspect, this invention provides a process for producing the phosphine compound represented by general formula [I]. More specifically, this invention provides a process for producing the phosphine compound [I], which comprises yielding the phosphine compound [I] by:

a process comprising:

Step 1a: reacting a halide compound represented by general formula [II]:

(wherein $Z_1$ means a cyclic group and $X_1$ means a halogen atom), a dihalophosphine compound represented by general formula [III]:

(wherein $Z_2$ means a cyclic group and $X_2$ and $X_3$ each means a halogen atom) and a methoxyaryl-metal magnesium halide represented by general formula [IV]:

(wherein $X_4$ means a halogen atom and Ar means an arylene group) to obtain a methoxyarylphosphine compound represented by general formula [V]:

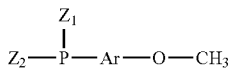
[V]

(wherein $Z_1$, $Z_2$ and Ar have the same meanings as defined above);

Step 2: reacting the methoxyarylphosphine compound [V] obtained in Step 1a above with an oxidizing agent to obtain a methoxyarylphosphine oxide compound represented by general formula [VI]:

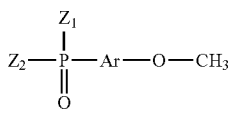
[VI]

(wherein $Z_1$, $Z_2$ and Ar have the same meanings as defined above);

Step 3: demethylating the methoxyarylphosphine oxide compound [VI] obtained in Step 2 above with a demethylating reagent to obtain a hydroxyarylphosphine oxide compound represented by general formula [VII]:

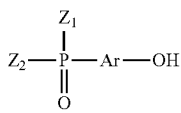
[VII]

(wherein $Z_1$, $Z_2$ and Ar have the same meanings as defined above);

Step 4: reacting the hydroxyarylphosphine oxide compound [VII] obtained in Step 3 above with a borane compound to obtain a hydroxyarylphosphine borane compound represented by general formula [VIII]:

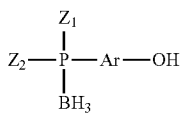
[VIII]

(wherein $Z_1$, $Z_2$ and Ar have the same meanings as defined above);

Step 5: reacting the hydroxymethoxyarylphosphine borane compound [VIII] obtained in Step 4 above with a halide compound represented by general formula [IX]:

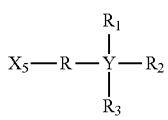
[IX]

(wherein $X_5$ means a halogen atom,

R means an aliphatic hydrocarbon group,

Y means phosphorus (P), nitrogen (N) or bismuth (Bi), and, $R_1$, $R_2$ and $R_3$ each means a cyclic group)
to obtain a phosphine borane compound represented by general formula [X]:

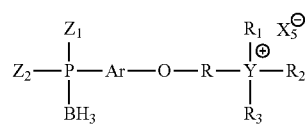
[X]

(wherein $Z_1$, $Z_2$, Ar, R, Y, $R_1$, $R_2$ and $R_3$ have the same meanings as defined above); and, Step 6: removing the protecting group from the phosphine borane compound [X] obtained in Step 5 above to yield a phosphine compound represented by general formula (I); or, a process comprising:

Step 1b: reacting the halide compound [II] above with a methoxyarylphosphine oxide compound [XI]:

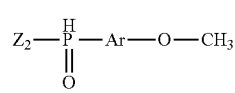
[XI]

(wherein $Z_2$ and Ar have the same meanings as defined above) to obtain the methoxyarylphosphine oxide compound represented by general formula [VI];

Step 3: demethylating the methoxyarylphosphine oxide compound [VI] obtained in Step 1b above with a demethylating reagent to obtain the hydroxyarylphosphine oxide compound [VII];

Step 4: reacting the hydroxyarylphosphine oxide compound [VII] obtained in Step 3 above with a borane compound to obtain the hydroxyarylphosphine borane compound [VIII];

Step 5: reacting the hydroxyarylphosphine borane compound [VIII] obtained in Step 4 above with the halide compound [IX] to obtain the phosphine borane compound [X]; and, Step 6: removing the protecting group from the phosphine borane compound [X] obtained in Step 5 above to yield the phosphine compound represented by general formula (I); or, a process comprising:

Step 7: reacting a halide compound represented by general formula [XII]:

[XII]

(wherein $X_6$ means a halogen atom and $R_1$ has the same meaning as defined above) with a halide compound represented by general formula [XIII]:

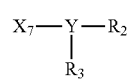
[XIII]

(wherein $X_7$ means a halogen atom and $R_2$ and $R_3$ have the same meanings as defined above) to obtain a compound represented by general formula [XIV]:

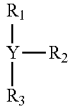
[XIV]

(wherein $R_1$, $R_2$ and $R_3$ have the same meanings as defined above);

Step 8: reacting the compound [XIV] obtained in Step 7 above with a dihalo-compound represented by general formula [XV]:

$$X_8-R-X_9 \quad [XV]$$

(wherein $X_8$ and $X_9$ each means a halogen atom) to obtain a halo-compound represented by general formula [XVI]:

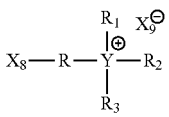
[XVI]

(wherein $R_1$, $R_2$, $R_3$, $X_8$ and $X_9$ have the same meanings as defined above)

Step 9: reacting the halo-compound [XVI] obtained in Step 8 above with the hydroxyarylphosphine borane compound represented by general formula [VIII] obtained in Step 4 above:

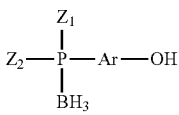
[VIII]

(wherein $Z_1$, $Z_2$ and Ar have the same meanings as defined above) to obtain a phosphine borane compound represented by general formula [XVII]:

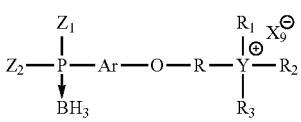
[XVII]

(wherein $Z_1$, $Z_2$, Ar, R, $R_1$, $R_2$, $R_3$ and $X_9$ have the same meanings as defined above); and, Step 10: deprotecting the phosphine borane compound [XVII] obtained in Step 9 above to yield a phosphine compound represented by general formula [XVIII]:

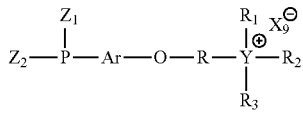
[XVIII]

(wherein $Z_1$, $Z_2$, Ar, R, R, $R_1$, $R_2$, $R_3$ and $X_9$ have the same meanings as defined above).

In a further embodiment, this invention provides a peroxide scavenger comprising the phosphine compound represented by general formula [I] and use of the same.

In a still further aspect, this invention provides a method for scavenging peroxides which comprises scavenging peroxides using the phosphine compound represented by general formula [I].

According to a preferable embodiment of the above aspect, this invention provides a method for scavenging peroxides, in which the peroxides are radical species such superoxide, hydroxyl radical, etc., or non-radical species such as hydrogen peroxide, singlet oxygen, or the like.

In a still further aspect, this invention provides oxidation products produced by oxidation of the phosphine compound represented by general formula [I]. More specifically, this invention provides a phosphinyl compound represented by general formula [I'], which is the oxidation product formed by oxidizing the phosphine compound represented by general formula [I]:

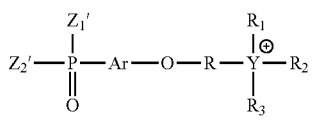
[I']

wherein $Z_1'$ and $Z_2'$ have the same meanings as defined for $Z_1$ and $Z_2$ above, respectively, with the proviso that when all of $R_1$, $R_2$ and $R_3$ are monocyclic hydrocarbon groups, either one of them is a cyclic group other than monocyclic hydrocarbon group, and when both $Z_1'$ and $Z_2'$ are monocyclic hydrocarbon groups, one of $R_1$, $R_2$ and $R_3$ means a cyclic group other than monocyclic hydrocarbon group.

The phosphine compound in accordance with this invention is a source for generating reactive oxygen. On the other hand, the phosphine compound can produce a functional molecule capable of visualizing the state of oxidative stress in mitochondria which are one of organelles most vulnerable to oxidative stress, whereby this invention provides an advantage that mechanisms of many diseases associated with oxidative stress can be uncovered.

BEST MODES FOR CARRYING OUT THE INVENTION

Figure 1:
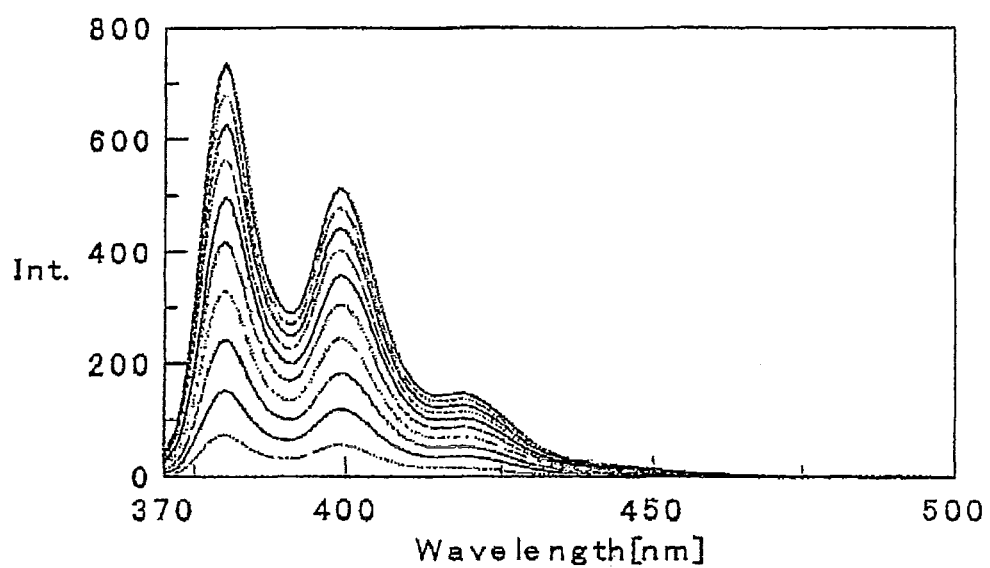
FIG. 1 shows time scale changes in fluorescence intensity resulting from the oxidation of MitoDPPP with hydrogen peroxide (EXAMPLE 4).

This invention relates to the phosphine compound represented by general formula [I]:

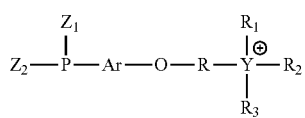

[I]

wherein:
$Z_1$ and $Z_2$ each represents a cyclic group;
Ar represents an arylene group;
R represents an aliphatic hydrocarbon group;
Y represents phosphorus (P), nitrogen (N) or bismuth (Bi); and,
$R_1$, $R_2$ and $R_3$ each represents a cyclic group.

In the phosphine compound [I] in accordance with this invention:
the cyclic groups shown by each of $Z_1$ and $Z_2$ are unsubstituted or substituted monocyclic hydrocarbon groups or polycyclic hydrocarbon groups or hetero-monocyclic groups or hetero-polycyclic groups;
the arylene group shown by Ar is an unsubstituted or substituted monocyclic hydrocarbon group or bicyclic hydrocarbon group;
the aliphatic hydrocarbon group shown by R is a linear or branched bivalent aliphatic hydrocarbon group having 1 to 8 carbon atoms;
the cyclic groups represented by $R_1$, $R_2$ and $R_3$, which may be the same or different, each represents a cationic group shown by which represents an unsubstituted or substituted monocyclic hydrocarbon group or polycyclic hydrocarbon group or hetero-monocyclic group or hetero-polycyclic group);
with the proviso that either one of the cyclic groups represented by $Z_1$ and $Z_2$ is a monocyclic hydrocarbon group or a hetero-monocyclic group and the other cyclic group is a polycyclic hydrocarbon group or a hetero-polycyclic group, and/or either one of the cyclic groups represented by $R_1$, $R_2$ and $R_3$ is a monocyclic hydrocarbon group or a hetero-monocyclic group, and the other cyclic group(s) is/are a polycyclic hydrocarbon group(s) or a hetero-polycyclic group(s).

According to a more preferable embodiment of this invention, in the phosphine compound represented by general formula [I], either one of the cyclic groups shown by $Z_1$ and $Z_2$ is a polycyclic hydrocarbon group or a hetero-polycyclic group and the other monocyclic group is a monocyclic hydrocarbon group or a hetero-monocyclic group, and all of the cyclic groups shown by $R_1$, $R_2$ and $R_3$ are monocyclic hydrocarbon groups or hetero-monocyclic groups; or, in all of the cyclic groups shown by $Z_1$ and $Z_2$, the monocyclic group is a monocyclic hydrocarbon group or a hetero-monocyclic group, either one of the cyclic groups shown by $R_1$, $R_2$ and $R_3$ is a polycyclic hydrocarbon group or a hetero-polycyclic group, and the other cyclic groups are monocyclic hydrocarbon groups or hetero-monocyclic groups.

In more detail, preferable examples of the cyclic groups shown by $Z_1$ and $Z_2$ in the phosphine compound represented by general formula [I] above are as follows: the monocyclic hydrocarbon group includes, for example, phenyl, etc.; the polycyclic hydrocarbon group includes a bicyclic hydrocarbon group such as indanyl, indenyl, pentalenyl, azulenyl, naphthyl, tetrahydronaphthyl, etc.; a tricyclic hydrocarbon group, e.g., anthracenyl, fluorenyl, phenalenyl, phenanthrenyl, etc.; a tetracyclic hydrocarbon group, e.g., pyrenyl, naphthacenyl, chrysenyl, etc.; a pentacyclic hydrocarbon group, e.g., perylenyl, picenyl, pentacenyl, etc.; a hexacyclic hydrocarbon group, e.g., naphthobyrenyl, etc.; or a heptacyclic hydrocarbon group, e.g., coronenyl, etc.; and, in the heterocyclic group, the hetero-monocyclic group includes a N-containing hetero-monocyclic group, e.g., pyrrolyl, imidazolyl, pyrazolyl, pyridyl, piperidyl, triazinyl, etc.; an O-containing hetero-monocyclic group, e.g., furanyl, pyranyl, etc.; a S-containing hetero-polycyclic group, e.g., thiophenyl, etc.; and a N/O/S-containing hetero-monocyclic group, e.g., oxazolyl, thiazolyl, morpholinyl, etc.; and, the hetero-polycyclic group includes a N-containing hetero-polycyclic group such as a N-containing hetero-bicyclic group, e.g., indolyl, indolinyl, quinolinyl, isoquinolinyl, quinazolinyl, quinoxalinyl, naphthyridinyl, puteridinyl, purinyl, etc.; and a N-containing hetero-tricyclic group, e.g., acridinyl, carbazolyl, phenanthridinyl, phenazinyl, benzoisoquinolinyl, etc.; an O-containing hetero-polycyclic group such as an O-containing hetero-bicyclic group, e.g., benzofuranyl, chromanyl, chromenyl, isochromanyl, etc., and an O-containing hetero-tricyclic group, e.g., xanthenyl, etc.; a S-containing hetero-polycyclic group such as a S-containing hetero-tricyclic group, e.g., dithianaphthyl, etc., a S-containing hetero-tricyclic group, e.g., thianthrenyl, etc.; and a N/O/S-containing hetero-polycyclic group, e.g., pyridoxazolyl, thienofuranyl, phenoxazinyl, phenothiazinyl, pyrazoloxazolyl, etc. These cyclic groups may optionally have substituents including a lower aliphatic hydrocarbon group having 1 to 6 carbon atoms, e.g., methyl, ethyl, propyl, isopropyl, etc.

The arylene group shown by Ar is phenylene, naphthalene, etc. The linear or branched bivalent aliphatic hydrocarbon group shown by R is methylene, ethylene, propylene, isopropylene, butylene, methylbutylene, etc.

In the cyclic groups represented by $R_1$, $R_2$ and $R_3$ of the cationic group shown by A, the monocyclic hydrocarbon group is, e.g., phenyl, etc.; the polycyclic hydrocarbon group includes a bicyclic hydrocarbon group, e.g., indanyl, indenyl, pentalenyl, azulenyl, naphthyl, tetrahydronaphthyl, etc.; a tricyclic hydrocarbon group, e.g., anthracenyl, fluorenyl, phenalenyl, phenanthrenyl, etc.; a tetracyclic hydrocarbon group, e.g., pyrenyl, naphthacenyl, chrysenyl, etc.; a pentacyclic hydrocarbon group, e.g., perylenyl, picenyl, pentacenyl, etc.; a hexacyclic hydrocarbon group, e.g., naphthobyrenyl, etc.; or a heptacyclic hydrocarbon group, e.g., coronenyl, etc.; the hetero-monocyclic group in the heterocyclic group includes a N-containing hetero-monocyclic group, e.g., pyrrolyl, imidazolyl, pyrazolyl, pyridyl, piperidyl, triazinyl, etc.; an O-containing hetero-monocyclic group, e.g., furanyl, pyranyl, etc.; a S-containing hetero-polycyclic group, e.g., thiophenyl, etc.; and a N/O/S-containing hetero-monocyclic group, e.g., oxazolyl, thiazolyl, morpholinyl, etc.; and, the hetero-polycyclic group includes a N-containing hetero-polycyclic group such as a N-containing hetero-bicyclic group, e.g., indolyl, indolinyl, quinolinyl, isoquinolinyl, quinazolinyl, quinoxalinyl, naphthyridinyl, puteridinyl, purinyl, etc.; a N-containing hetero-tricyclic group, e.g., acridinyl, carbazolyl, phenanthridinyl, phenazinyl, benzoisoquinolinyl, etc.; the O-containing hetero-polycyclic group includes an O-containing hetero-bicyclic group, e.g., benzofuranyl, chromanyl, chromenyl, isochromanyl, etc., and an O-containing hetero-tricyclic group, e.g., xanthenyl, etc.; the S-containing hetero-polycyclic group includes a S-containing hetero-tricyclic group, e.g., dithianaphthyl, etc., a S-containing hetero-tricyclic group, e.g., thianthrenyl, etc.; and a N/O/S-containing hetero-polycyclic group, e.g., pyridoxazolyl, thienofuranyl, phenoxazinyl, phenothiazinyl, pyrazoloxazolyl, etc. These cyclic groups may optionally have substituents including a lower aliphatic hydrocarbon group having 1 to 6 carbon atoms, e.g., methyl, ethyl, propyl, isopropyl, etc.

Since the phosphine compound represented by general formula [I] described above is in a cationic state, the compound is preferably in such a configuration that binds to an anion. The cation includes halogen ions such as chlorine, bromine, iodine, etc. As a natural consequence, these anion-bound compounds are also included as one embodiment of this invention.

The phosphine compound [I] in accordance with this invention per se can be produced by known processes in the art. The process for production of the compound is described below in more detail.

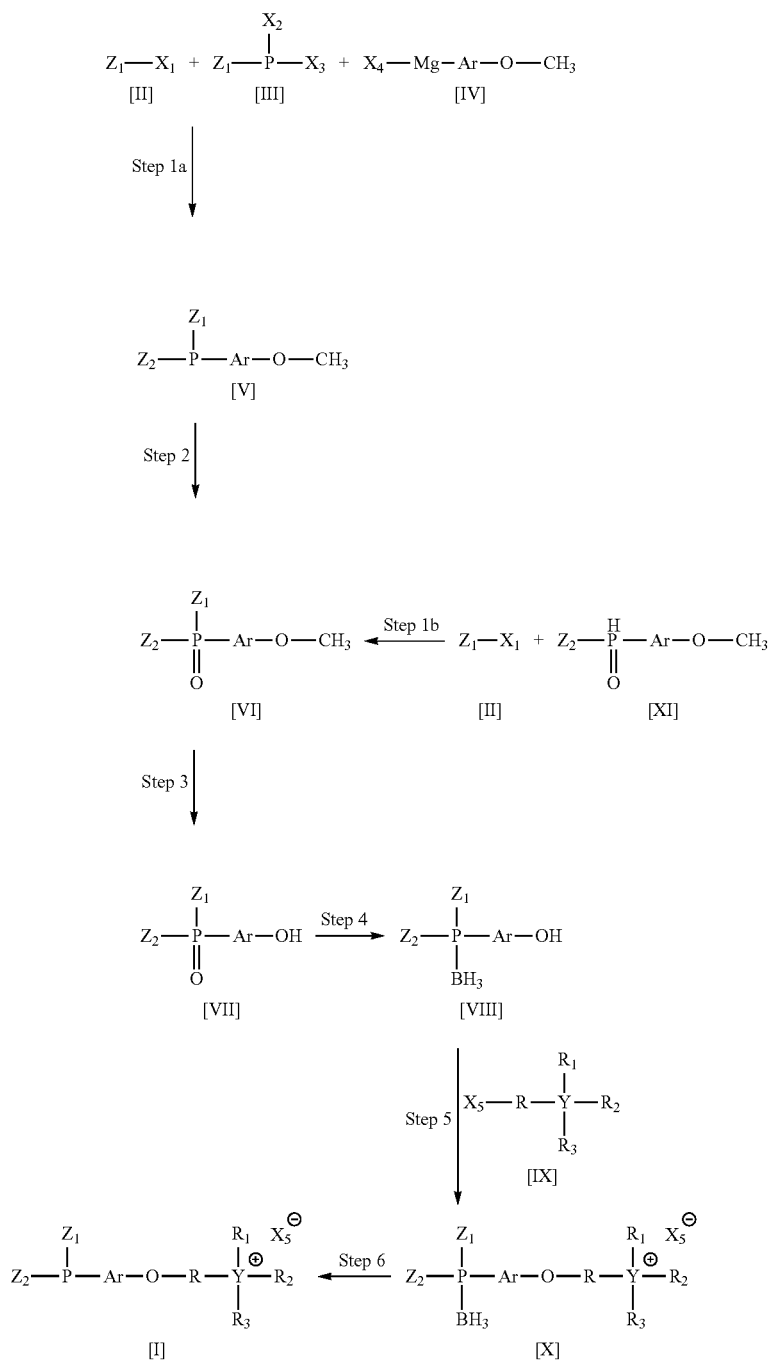

As shown in the reaction scheme above, Step 1a is a step of reacting halide compound [II], dihalo-phosphine compound [III] and methoxyaryl-metal magnesium halide [IV] to give the methoxyarylphosphine compound [V].

The halogen atom in halide compound [II] used in Step 1 includes, for example, bromine, iodine, chlorine, etc. Examples of halide compound [II] are phenyl bromide, tolyl chloride, naphthyl bromide, anthracenyl bromide, pyrenyl bromide, perylenyl bromide, etc.

Examples of dihalophosphine compound [III] are dichlorophenylphosphine, dibromophenylphosphine, diiodophenylphosphine, etc. The substituent for dihalophosphine compound [III] includes an aliphatic hydrocarbon group having 1 to 6 carbon atoms, preferably 1 to 3 carbon atoms, e.g., methyl, ethyl, propyl, isopropyl, etc.

Examples of methoxyaryl-metal magnesium halide [IV] include methoxyphenyl magnesium chloride, methoxyphenyl magnesium bromide, methoxyphenyl magnesium iodide, etc. The substituent includes an aliphatic hydrocarbon group having 1 to 6 carbon atoms, preferably 1 to 6 carbon atoms, e.g., methyl, ethyl, propyl, isopropyl, etc. The number and position of the substituent are not particularly limited but may be optional unless the substituent interferes the reaction.

In Step 1, the reaction is preferably carried out in a solvent. Examples of the solvent which can be used are ethers such as diethyl ether, tetrahydrofuran, etc. The reaction temperature ranges from, e.g., 0° C. to −100° C., and preferably −40° C. to −80° C. The reaction time is, for example, about 1 to 24 hours, and preferably about 5 to 15 hours.

Step 2 is an oxidation reaction for methoxyarylphosphine compound [V] obtained in Step 1a to give methoxyarylphosphine oxide compound [VI]. This oxidation reaction can be performed in a solvent using an oxidizing agent. Example of the oxidizing agent which can be employed are hydrogen peroxide, potassium hydrogen monopersulfate, etc. The solvent which can be used includes an organic solvent such as an alkyl halide, e.g., dichloromethane, chloroform, etc. The reaction temperature ranges from room temperature to about 60° C. and preferably from 40° C. to 45° C. The reaction time is about 10 minutes to an hour, and preferably, about 15 to 25 minutes.

As shown in the reaction scheme described above, methoxyarylphosphine oxide compound [VI] can also be produced in Step 1b. That is, compound [VI] can also be produced by reacting halide compound [II] described above with methoxyarylphosphine oxide [XI]. Preferably, the reaction in Step 1b is carried out in a solvent such as dimethylsulfoxide, dimethylformamide, etc., in the presence of a palladium compound such as palladium acetate, etc., 1,3-bis(diphenylphosphino)propane and an amine such as diisopropylethylamine, etc. The reaction temperature is under heating, for example, at room temperature to 160° C., preferably at 150° C. The reaction time is about 10 to 24 hours, and preferably, about 12 to 18 hours.

Step 3 is a reaction for deprotecting methoxyarylphosphine oxide compound [VI] obtained in Step 2 to give hydroxyarylphosphine oxide compound [VII]. According to this deprotecting reaction, methoxy of the methoxyphenyl group in the methoxyarylphosphine oxide compound [VI] is deprotected and converted into hydroxy. Advantageously, the deprotecting reaction is carried out in a solvent using a deprotecting agent. The deprotecting agent which can be employed includes, for example, a demethylating reagent such as borane tribromide, etc. The solvent which can be used includes a non-protonic solvent, for example, an alkyl halide such as dichloromethane, dichloroethane, chloroform, etc.

The reaction temperature ranges from about −50° C. to 0° C., and preferably about −20° C. to −10° C. The reaction time is about 1 to 24 hours, and preferably, about 10 to 20 hours.

Step 4 is a reaction of hydroxyarylphosphine oxide compound [VII] obtained in Step 3 described above with a protecting reagent for introducing a protecting group to give hydroxyarylphosphine borane compound [VIII]. In the reaction of this step, the dicyclic group-substituted hydroxyarylphosphine oxide compound [VII] is reacted with the protecting reagent in a solvent to introduce the borane protecting group. The protecting reagent which can be used in this step includes a borohydride compound, e.g., monoborane, etc. Examples of the solvent which can be used are an alkyl amine such as triethylamine, tributylamine, etc. The reaction temperature ranges from about −50° C. to 200° C., and preferably about −20° C. to 150° C. The reaction time is about 10 minutes to 24 hours, and preferably about 30 minutes to 20 hours.

Step 5 is an alkylation step for reacting hydroxyarylphosphine borane compound [VIII] obtained in Step 4 described above with the substituted alkyl halide [IX] to give phosphine borane compound [X]. This ether bond forming reaction is advantageously carried out in an organic solvent such as formamide, e.g., dimethylformamide, etc., at a reaction temperature of about −50° C. to 0° C., preferably about −20° C. to 0° C. for about 10 minutes to 24 hours, preferably about 30 minutes to 20 hours, in the presence of a base, e.g., sodium hydride, etc.

Step 6 is a step of deprotecting the borane protective group of the tri-substituted phosphine borane compound [X] obtained in Step 5 to give phosphine compound [I]. This deprotection reaction is advantageously carried out in a solvent using the deprotecting agent. The deprotecting agent includes a deboranating agent, e.g., diethylamine, diisopropylethylamine, etc. The solvent which can be used includes a non-protonic solvent, for example, an alkyl halide such as dichloromethane, dichloroethane, etc. The reaction temperature ranges from about 0° C. to 60° C., and preferably about 30° C. to 40° C. The reaction time is, for example, about 1 to 24 hours, and preferably about 10 to 15 hours.

The phosphine compound [I] in accordance with this invention can also be produced by the process consisting of the following steps. In the reaction scheme described below, the phosphine compound [I] is shown by general formula [XVIII].

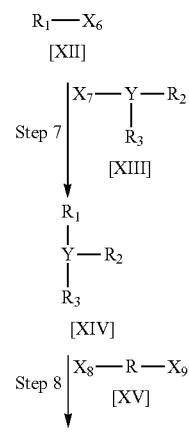

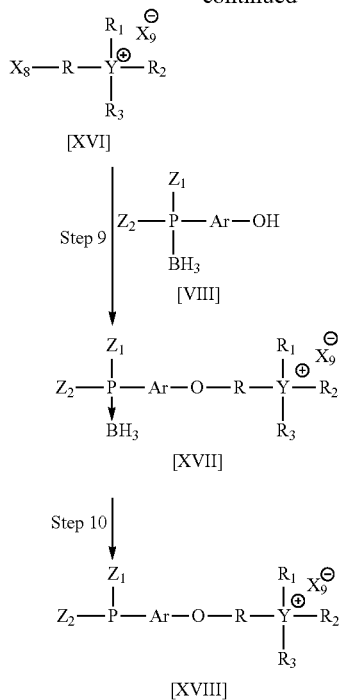

Step 7 is a step of reacting halide compound [XII] and monohalo-phosphine compound [XIII] in the presence of an alkyllithium, e.g., butyllithium to give triarylphosphine compound [XIV].

The halogen atom in halide [XII] used in Step 7 includes, for example, bromine, iodine, chlorine, etc. Examples of halide compound [XII] are phenyl bromide, tolyl chloride, naphthyl bromide, anthracenyl bromide, pyrenyl bromide, perylenyl bromide, etc.

Examples of monohalo-phosphine compound [XIII] include chlorophenylphosphine, bromophenylphosphine, iodophenylphosphine, etc. The substituent for halophosphine compound [XIII] includes an aliphatic hydrocarbon group having 1 to 6 carbon atoms, preferably 1 to 3 carbon atoms, e.g., methyl, ethyl, propyl, isopropyl, etc. The number and position of the substituent are not particularly limited but may be optional unless the substituent interferes the reaction.

The reaction is advantageously carried out in a solvent. Examples of the solvent which can be used are ethers such as diethyl ether, tetrahydrofuran, etc. The reaction temperature ranges from, e.g., 0° C. to −100° C., and preferably −40° C. to −80° C. The reaction time is, for example, 1 to 24 hours, and preferably about 5 to 15 hours.

Step 8 is a step of reacting alkyl dihalide [XVI] and triarylphosphine [XIV] to give the substituted alkyl halide [XVI]. This alkylation reaction is advantageously carried out in an organic solvent such as an aromatic hydrocarbon, e.g., toluene, etc., at the reaction temperature of about −50° C. to 200° C., preferably about −20° C. to 150° C. for about 10 minutes to 24 hours, preferably about 30 minutes to 20 hours.

Step 9 is an alkylation step of reacting hydroxyarylphosphine borane compound [VIII] obtained in Steps 1a, 2, 3 and 4 described above with the substituted alkyl halide [XVI] to give phosphine borane compound [XVII]. This ether bond forming reaction is advantageously carried out in an organic solvent such as formamide, e.g., dimethylformamide, etc., at the reaction temperature of about −50° C. to 0° C., preferably about −20° C. to 0° C. for the reaction time of about 10 minutes to 24 hours, preferably about 30 minutes to 20 hours, in the presence of a base, e.g., sodium hydride, etc.

Step 10 is a step of deprotecting the borane protecting group from the tri-substituted phosphine borane compound [XVIII] obtained in Step 9. This deprotection reaction is advantageously carried out in a solvent using the deprotecting agent. The deprotecting agent includes a deboranating agent, e.g., diethylamine, diisopropylethylamine, etc. The solvent which can be used includes a non-protonic solvent, for example, an alkyl halide such as dichloromethane, dichloroethane, etc. The reaction temperature ranges from about 0° C. to 60° C., and preferably about 30° C. to 40° C. The reaction time is, for example, about 1 to 24 hours, and preferably about 10 to 15 hours.

Phosphine compound [I] in accordance with this invention is, once oxidized, rapidly converted into phosphonium oxide salt [I'], whereby the fluorescence intensity increases. It has been confirmed by double-staining of phosphonium oxide salt [I'] using a mitochondria-selective fluorescent marker that phosphonium oxide salt [I'] is localized in mitochondria. When phosphine compound [I] was oxidized with hydrogen peroxide and tert-butoxyhydroperoxide (tBHP) in an aqueous solution, it was confirmed that the fluorescence intensity increased with both oxidants. On the other hand, when phosphine compound [I] localized in mitochondria was likewise oxidized, the fluorescence of phosphonium oxide salt [I'] was observed only when tBHP was used.

Phosphine compound [I] is oxidized to give phosphonium oxide salt [I'] as shown above. More specifically, phosphonium oxide salt [I'] is the compound represented by general formula [I']:

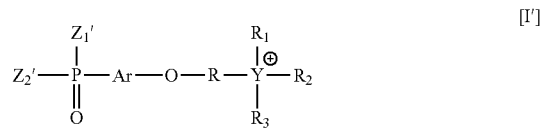

(wherein $Z_1'$ and $Z_2'$ have the same meanings as defined for $Z_1$ and $Z_2$ above, respectively, with the proviso that when all of $R_1$, $R_2$ and $R_3$ represent monocycle hydrocarbon groups, either one of them is a cyclic group other than monocyclic hydrocarbon group, and when both $Z_1'$ and $Z_2'$ represent monocyclic hydrocarbon groups, one of $R_1$, $R_2$ and $R_3$ means a cyclic group other than monocyclic hydrocarbon group).

These results reveal that phosphine compound [I] of this invention is localized in living cells, especially in mitochondria and can scavenge peroxides such as reactive oxygen species, etc. generated in mitochondria. Accordingly, the phosphine compound [I] of this invention is localized in mitochondria, it is capable of scavenging peroxides, and hence can be used as a mitochondrial peroxide scavenger.

Example 1

The reaction scheme of [3-(4-phenoxyphenylphosphinopyrenylphosphino)propyl]triphenylphosphonium iodide [Ia] (MitoDPPP) in accordance with this invention is as follows.

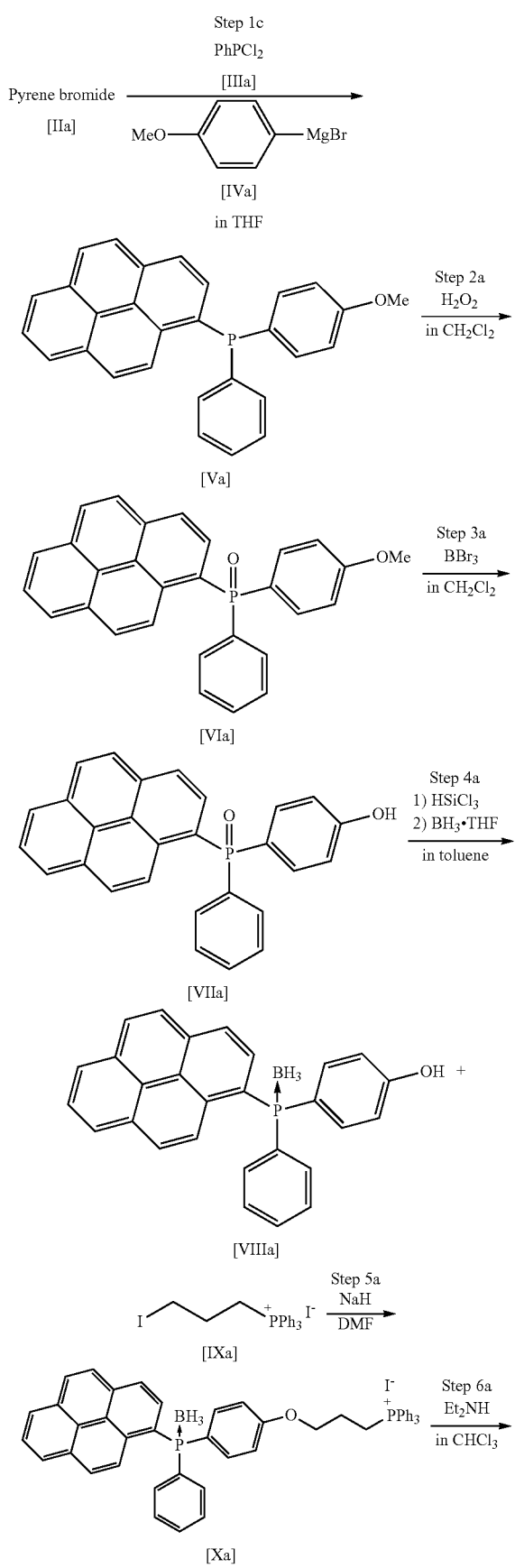

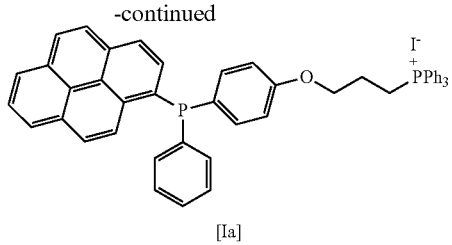

[Ia]

Each step in the reaction scheme described above is explained in detail hereinbelow.

Step 1c: Synthesis of 4-methoxyphenylphenylpyrenylphosphine [Va]

Pyrene bromide [IIa] (3.28 g, 15 mmol) was dissolved in 70 mL of THF, and n-BuLi (6.11 mL, 2.7 M, 16.5 mmol, 1.1 eq) was added dropwise to the solution at −78° C. over 15 minutes. The mixture was stirred for 3 hours. This reaction product was dropwise added over 15 minutes to dichlorophenylphosphine [IIIa] (2.03 mL, 15 mmol, 1 eq) dissolved in 6 mL of THF (−78° C.). After stirring overnight, 4-methoxyphenyl magnesium bromide [IVa] (45 mL, 0.5 M, 22.5 mmol, 1.5 eq) was dropwise added over 15 minutes to the reaction mixture at −78° C. After stirring the mixture for 6 hours, the reaction was quenched with 50 mL of saturated ammonium chloride aqueous solution. The inorganic salt produced was removed by suction filtration, followed by extraction with dichloromethane (100 mL×3). The organic layer was dried over sodium sulfate and concentrated on an evaporator. The residue was purified by column chromatography using a developing solvent (dichloromethane:hexane=1:2). The product was obtained as pale yellow crystals in 32% yield. The pale yellow crystals were identified by $^1$H-NMR, $^{31}$P-NMR, $^{13}$C-NMR, H—H COSY and C—H COSY.

$^1$H-NMR (CDCl$_3$, 400 MHz) δ 3.78 (s, 3H), 6.89 (d, J=8.8 Hz, 2H), 7.28-7.34 (m, 7H), 7.54 (dd, J=8.0, 4.4 Hz, 1H), 7.98-8.10 (m, 5H), 8.17-8.20 (m, 2H), 8.73 (dd, 8.0, 4.4 Hz, 1H).

$^{31}$P-NMR (CDCl$_3$, 162 MHz) δ −14.23.

$^{13}$C-NMR (CDCl$_3$, 100 Hz) δ 114.36, 114.38, 114.62, 114.71, 124.78, 124.80, 124.88, 124.93, 124.99, 125.54, 125.60, 125.74, 125.81, 126.29, 127.29, 127.36, 127.64, 127.95, 127.98, 128.29, 128.49, 128.55, 128.78, 128.83, 128.49, 130.98, 131.09, 131.55, 131.94, 132.26, 132.41, 132.43, 133.94, 134.03, 134.13, 134.26, 134.76, 134.97, 136.07, 136.29, 137.68, 137.78, 160.69.

Step 2a: Synthesis of 4-methoxyphenylphenylpyrenylphosphine oxide [VIa]

Pyrenylphenyl-4-methoxyphenylphosphine [Va] (1.68 g, 4.03 mmol) was dissolved in 25 mL of chloroform, and 5 mL of hydrogen peroxide was slowly added dropwise to the solution. The mixture was stirred for 5 minutes and then the reaction was quenched with 25 mL of 10% sodium thiosulfate. The mixture was extracted with chloroform (20 mL×3). The organic layer was dried over sodium sulfate and concentrated on an evaporator to give white crystals in 97% yield. The white crystals obtained were identified by $^1$H-NMR, $^{31}$P-NMR and $^{13}$C-NMR.

$^1$H-NMR (CDCl$_3$, 400 MHz) δ 3.82 (s, 3H), 6.97 (d, J=11.2 Hz, 2H), 7.43-7.49 (m, 2H), 7.52-7.56 (m, 1H), 7.60-7.78 (m, 5H), 8.00-8.08 (m, 4H), 8.15-8.23 (m, 3H), 8.94 (d, J=9.6 Hz, 1H).

$^{31}$P-NMR (CDCl$_3$, 162 MHz) δ 33.93.

$^{13}$C-NMR (CDCl$_3$, 100 Hz) δ 114.37, 114.50, 123.68, 123.82, 124.03, 124.43, 125.14, 125.27, 125.32, 125.37, 126.35, 126.59, 126.67, 127.36, 128.74, 128.86, 129.06, 130.01, 130.66, 131.24, 131.35, 131.48, 131.98, 132.01, 132.33, 132.43, 133.51, 134.24, 134.28, 134.35, 134.38, 134.55, 162.66, 162.69.

Step 3a: Synthesis of 4-methoxyphenylphenylpyrenylphosphine oxide [VIIa]

Pyrenylphenyl-4-methoxyphenylphosphine oxide [VIa] (1.7 g, 3.9 mmol) was dissolved in 100 mL of dichloromethane. Borane tribromide (11 mL, 11 mmol, 4 eq) was added dropwise to the solution at −78° C. After stirring the mixture for 18 hours, the reaction was quenched with 40 mL of H$_2$O. The white crystals thus produced were filtered by suction. The resulting crystals were dried overnight in a drying pistol to give white crystals in 94% yield. The white crystals obtained were identified by $^1$H-NMR and $^{31}$P-NMR.

$^1$H-NMR (DMSO-d$_6$, 400 MHz) δ 6.92 (d, J=10.8 Hz, 2H), 7.40-7.45 (m, 2H), 7.52-7.61 (m, 5H), 7.69 (dd, J=12.0, 7.6 Hz, 1H), 8.11-8.40 (m, 7H), 8.83 (d, J=9.2 Hz, 1H), 10.34 (br).

$^{31}$P-NMR (DMSO-d$_6$, 162 MHz) δ 31.10.

Step 4a: Synthesis of 4-hydroxyphenylphenylpyrenylphosphine borane [VIIIa]

A solution of triethylamine (1.79 mL, 13 mmol, 4 eq) in 100 mL of toluene was added dropwise to pyrenylphenyl-4-methoxyphenylphosphine oxide [VIIa] (1.2 g, 3.1 mmol), and the mixture was stirred on ice. Trichlorosilane (1.2 mL, 12 mmol, 4 eq) was added dropwise to the mixture over 10 minutes. The mixture was then refluxed at 110° C. After stirring for 18 hours, borane-THF complex (3.00 mL, 3.1 mmol, 1 eq) was dropwise added over 10 minutes to the mixture. After stirring the mixture for 15 minutes, the reaction was quenched with 5 mL of methanol. The white precipitates were removed by suction filtration. The filtrate was concentrated on an evaporator to give pale yellow crystals in 88% yield. The pale yellow crystals obtained were subjected to column chromatography using a developing solvent (ethyl acetate:hexane=1:2) to give pale yellow crystals. The pale yellow crystals were identified by $^1$H-NMR and $^{31}$P-NMR.

$^1$H-NMR (CDCl$_3$, 400 MHz) δ 6.88 (d, 8.4 Hz, 2H), 7.40-7.44 (m, 2H), 7.49-7.58 (m, 3H), 7.65-7.74 (m, 3H), 7.96-8.06 (m, 4H), 8.11-8.24 (m, 3H), 8.40 (d, J=9.2 Hz, 1H).

$^{31}$P-NMR (CDCl$_3$, 162 MHz) δ 20.40 (br).

$^{13}$C-NMR (CDCl$_3$, 100 Hz) δ 116.41, 116.51, 119.96, 120.58, 122.39, 122.94, 124.38, 124.42, 124.53, 125.36, 125.44, 126.37, 126.61, 126.67, 126.72, 127.35, 128.35, 129.13, 129.24, 129.74, 130.02, 130.55, 130.61, 131.27, 131.45, 131.47, 131.96, 13204, 133.43, 133.48, 133.53, 133.57, 133.96, 133.98, 135.69, 135.79, 158.66, 158.68. IR 830.91, 1102.58, 1175.52, 1435.70, 1500.34, 1580.50, 2375.59, 3405.33.

Step 5a: Synthesis of Phosphine Borane [Xa]

Sodium hydride [VIIIa] (192 mg, 2.9 mmol, 1.1 eq) was washed with hexane (1 mL×3) in a glo box, and 5 mL of DMF was dropwise added thereto. The mixture was stirred for 10 minutes. A solution of pyrenylphenyl-4-phenoxyphosphine borane (1.14 g, 2.7 mmol, 1 eq) in 5 mL of DMF was added dropwise to the mixture over 5 minutes. After stirring for 3 hours, a solution of iodopropane triphenylphosphonium iodide [IXa] (1.51 g, 2.7 mmol, 1 eq) in 5 mL of DMF was dropwise added over 5 minutes to the mixture at −15° C. After stirring for 6 hours, the reaction solution changed from orange turbid liquid to yellow transparent solution. Then, the reaction was quenched with 5 mL of saturated ammonium chloride aqueous solution. The organic layer was extracted with dichloromethane (10 mL×3), dried over sodium sulfate and concentrated on an evaporator to give yellow oil. The yellow oil was purified by column chromatography using a developing solvent (dichloromethane:ethyl acetate=3:7). The yellow crystals obtained were dissolved in a small quantity of dichloromethane. When ethyl acetate was added to the solution, white precipitates were formed. The upper layer was removed by decantation and the residue was suctioned by an oil pump to give white crystals in 33% yield. The white crystals obtained were identified by $^1$H-NMR, $^{31}$P-NMR and ESI-MS.

$^1$H-NMR (CDCl$_3$, 400 MHz) δ 2.16-2.18 (m, 2H), 4.05-4.13 (m, 2H) 4.38-4.41 (m, 2H), 6.92 (d, J=8.0 Hz, 2H), 7.27-7.44 (m, 2H), 7.49-7.57 (m, 3H), 7.65-7.86 (m, 18H), 7.95-8.08 (m, 4H), 8.12-8.22 (m, 3H), 8.39 (d, J=9.2 Hz, 1H).

$^{31}$P-NMR (CDCl$_3$, 162 MHz) δ 20.26 (br), 25.90. $^{13}$C-NMR (CDCl$_3$, 100 Hz) δ19.95 (d, J$_{cp}$=52.60 Hz), 23.01 (s), 66.99 (d, J$_{cp}$=16.80 Hz), 115.48, 115.59, 117.87, 118.73, 120.13, 120.76, 122.41, 122.96, 124.38, 124.49, 124.59, 125.32, 125.41, 126.35, 126.56, 126.61, 126.68, 127.41, 128.31, 129.13, 129.23, 129.69, 129.93, 130.51, 130.67, 130.80, 131.26, 131.45, 131.47, 132.01, 132.10, 133.36, 133.43, 133.52, 133.87, 133.97, 135.32, 135.35, 135.41, 135.51, 160.97, 160.99. IR 688.37, 738.36, 1105.66, 1247.54, 1435.83, 1498.61, 1592.29, 2377.83.

ESI-MS (C$_{49}$H$_{42}$BOP$_2^+$): Calcd.: 719. Found: 721.

Elemental analysis (C$_{49}$H$_{42}$BIOP$_2$): Calcd.: C, 69.52; H, 5.00. Found: C, 69.37; H, 5.28.

Step 6a: Synthesis of [3-(4-phenoxyphenylphosphinopyrenylphosphino)propyl]triphenylphosphonium iodide [Ia]

[Pyrenylphenyl-4-phenoxyphosphineborane]triphenylphosphonium dide [Xa] (167 mg, 0.21 mmol) was dissolved in 1 mL of chloroform, and diethylamine (102 μL, 0.84 mmol, 4 eq) was added dropwise to the solution. The mixture was stirred overnight at 40° C. on a water bath. The solvent was concentrated on an evaporator. The residue was purified by column chromatography using a developing solvent (dichloromethane:methanol=13:1) to give white crystals in 51% yield. The white crystals were identified by $^1$H-NMR and $^{31}$P-NMR.

$^1$H-NMR (CDCl$_3$, 400 MHz) δ 2.15-2.19 (m, 2H), 4.08-4.15 (m, 2H), 4.34 (t, J=5.6 Hz, 2H), 6.82 (d, J=8.8 Hz, 2H), 7.21-7.33 (m, 7H), 7.52 (dd, J=7.6, 4.4 Hz, 1H), 7.63-7.87 (m, 15H), 7.97-8.09 (m, 5H), 8.16-8.19 (m, 2H), 8.71 (dd, J=9.2 Hz, 4.4 Hz, 1H). $^{31}$P-NMR (CDCl$_3$, 162 MHz) δ −13.76, 26.07.

$^{13}$C-NMR (CDCl$_3$, 100 Hz) δ 19.96 (d, J$_{cp}$=51.9 Hz), 23.15 (s), 66.75 (d, J$_{cp}$=16.0 Hz), 115.22, 115.31, 118.05, 118.90, 124.76, 124.84, 124.89, 125.06, 125.50, 125.58, 125.70, 125.77, 126.26, 127.68, 127.74, 127.81, 127.90, 127.933, 128.25, 128.78, 128.85, 130.62, 130.74, 131.01, 131.06, 131.54, 131.91, 132.20, 132.34, 133.91, 134.01, 134.09, 134.18, 135.22, 135.25, 136.09, 136.30, 137.48, 137.58, 159.29. IR 687.78, 1110.48, 1241.25, 1434.81, 1588.94.
ESI-MS for C$_{49}$H$_{39}$OP$_2^+$: Calcd.: 705. Found: 705.
Example 2
EXAMPLE 2 shows the process for producing MitoPeDPP.
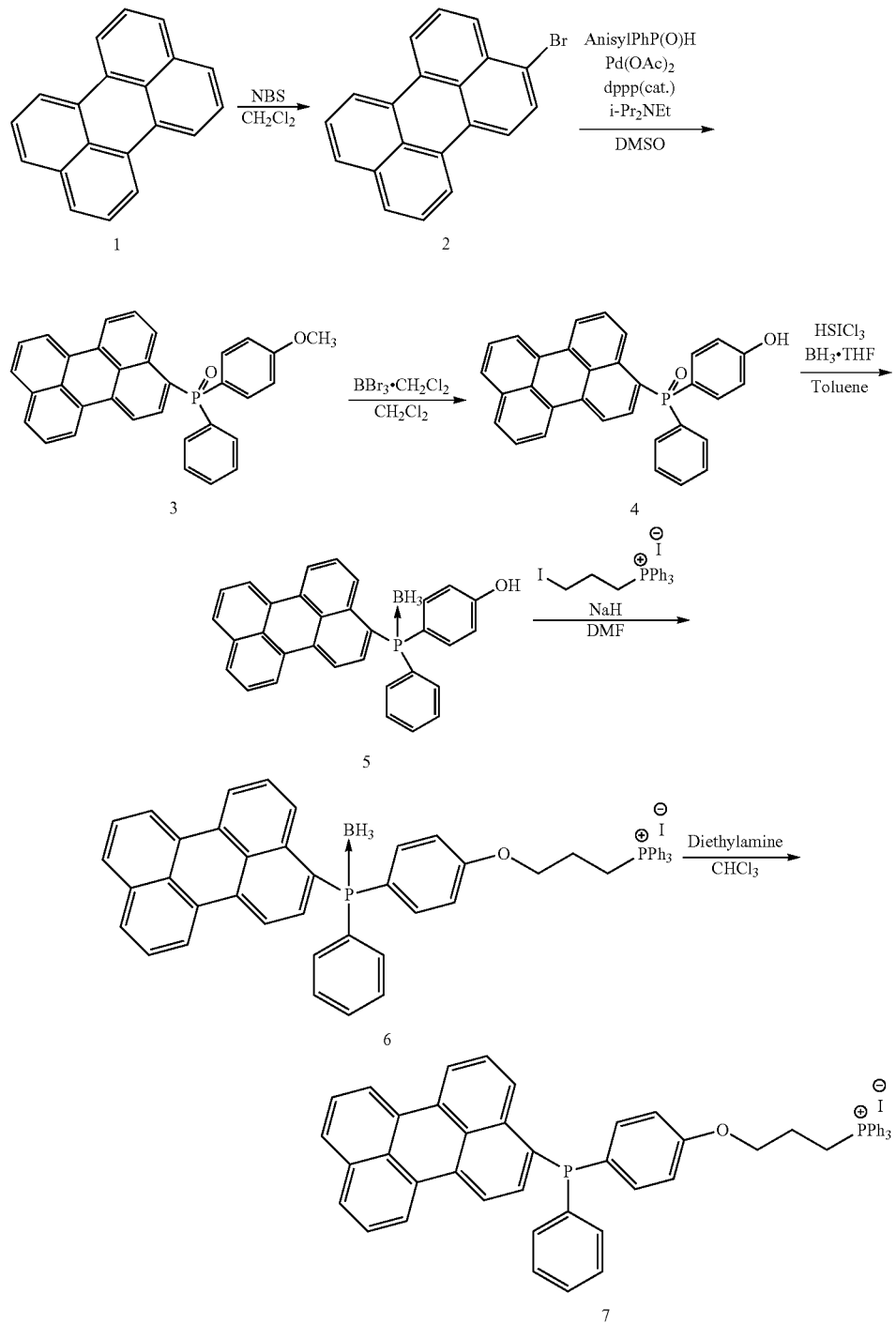
Scheme 1 Synthesis of MitoPeDPP

Synthesis of Perylene Bromide

After 3.0 g (11 mmol) of perylene was dissolved in 700 mL of dichloromethane, the solution was stirred for 5 minutes. To the solution, 2.11 g (12 mmol, 1.1 eq) of N-bromosuccinimide was dropwise added slowly at room temperature, followed by stirring overnight. The reaction solution was purified by silica gel column chromatography using a developing solvent adjusted to dichloromethane:hexane=1:1 to remove N-bromosuccinimide. After the solvent was concentrated, yellow crystals (yield 90%) were obtained. The compound was identified by $^1$H-NMR and ESI-MS.

$^1$H-NMR (CDCl$_3$, 400 MHz) δ 7.46-7.51 (m, 2H), 7.59 (t, J=4.4 Hz, 1H), 7.68-7.72 (m, 2H), 7.78-7.80 (m, 1H), 7.98-8.04 (m, 1H), 8.09-8.14 (m, 1H), 8.17-8.28 (m, 3H).

ESI-MS (C$_{20}$H$_{11}$Br): Calcd.: 330.00. Found: 331.9.

Synthesis of Anisylphenylphosphine Oxide

After 3.2 mL (40 mmol, 2 eq) of pyridine was added to 30 ml of hexane, 2.7 mL (20 mmol) of dichlorophenylphosphine was slowly added dropwise to the mixture. Then, 4.18 mL (40 mmol, 2 eq) of diethylamine was slowly added dropwise to the mixture, followed by reflux for 3 hours. After the solvent was removed, pale yellow oily substance was obtained (yield 60%).

The crude product obtained was dissolved in 35 mL of tetrahydrofuran, and the resulting solution was stirred on an ice bath of −15° C. for 15 minutes. Then 24 mL (12 mmol, 1 eq) of anisyl magnesium bromide was slowly added dropwise to the solution. After the mixture was stirred overnight, 15 mL of 2N hydrochloric acid aqueous solution was added dropwise to the mixture at room temperature. The reaction mixture was extracted with ether (30 mL×3), and the extract was dried over sodium sulfate. The solvent was removed to give crude anisylphenylphosphine oxide (yield 40%).

Synthesis of 4-methoxyphenylphenylperylenylphosphine oxide (3)

A solution containing 1.2 g (9.4 mmol, 4 eq) of diisopropylethylamine in 17 mL of DMSO was added dropwise to the mixture of 780 mg (2.35 mmol) of perylene bromide, 1.1 g (4.7 mmol, 2 eq) of anisylyphenylphosphine oxide, 53 mg (0.24 mmol, 0.05 eq) of palladium acetate and 99 mg (0.24 mmol, 0.05 eq) of 1,3-bis(diphenylphosphino)propane. The reaction temperature was elevated to 150° C., and the mixture was stirred overnight. The reaction was confirmed by TLC, and then 50 mL of ethyl acetate was added to dilute the mixture, followed by washing with H$_2$O and saturated NaCl aqueous solution (30 ml×3) for three times. The organic layer was dried over sodium sulfate and the solvent was removed to give pale yellow crystals. Purification was performed by silica gel column chromatography (dichloromethane:ethyl acetate=1:1) (yield 70%). The compound was identified by $^1$H-NMR, $^{31}$P-NMR, $^{13}$C-NMR, IR, ESI-MS and UV.

$^1$H-NMR (CDCl$_3$, 400 MHz) δ 3.86 (s, 3H), 6.99 (d, J=4.4 Hz, 2H), 7.24-7.29 (m, 1H), 7.30-8.06 (m, 12H), 8.08 (d, J=2 Hz, 1H), 8.20-8.24 (m, 3H), 8.49 (d, J=4.2 Hz, 1H). $^{31}$P-NMR (CDCl$_3$, 162 MHz) δ 33.60.

$^{13}$C-NMR (CDCl$_3$, 100 Hz) δ 55.59, 114.43, 114.56, 118.52, 118.67, 121.03, 121.19, 121.84, 124.32, 126.81, 127.09, 127.77, 127.83, 127.94, 128.44, 128.57, 128.67, 128.79, 128.91, 129.57, 130.37, 131.13, 131.83, 132.11, 132.29, 132.38, 133.78, 134.20, 134.32, 134.50, 134.61, 134.68, 135.61, 135.97, 162.78.

IR 758.72, 809.70, 117.79, 1170.46, 1254.81, 1501.34, 1595.92, 3048.39.

ESI-MS (C$_{33}$H$_{23}$O$_2$P+H): Calcd.: 483.15. Found: 483.11; UV: 427 nm, 453 nm.

Synthesis of 4-hydroxyphenylphenylperylenylphosphine oxide (4)

4-Methoxyphenylphenylperylenylphosphine oxide (400 mg, 0.83 mmol) was dissolved in 30 mL of dichloromethane, and borane tribromide (2.5 mL, 2.5 mmol, 4 eq) was added dropwise to the solution at −78° C. After stirring for 18 hours, 10 mL of H$_2$O was added to the mixture to terminate the reaction. Reddish brown precipitates thus formed were subjected to suction filtration. The crystals obtained were dried overnight in a drying pistol to give reddish brown crystals (yield 77%). The crystals obtained were identified by $^1$H-NMR, $^{31}$P-NMR, IR, ESI-MS and UV.

$^1$H-NMR (CDCl$_3$, 400 MHz) δ 6.92 (d, J=3.6 Hz, 2H), 7.21 (dd, J=3.8, 15 Hz, 1H), 7.41-7.63 (m, 10H), 7.84-7.90 (m, 2H), 8.35-8.42 (d, J=2 Hz, 5H), 10.24 (br, 1H).

$^{31}$P-NMR (CDCl$_3$, 162 MHz) δ 30.59. IR 757.64, 805.41, 118.60, 114.94, 1292.26, 1437.65, 1505.70, 1579.50, 3050.38.

ESI-MS (C$_{32}$H$_{21}$O$_2$P+K): Calcd.: 509.09. Found: 509.12. UV: 427 nm, 453 nm.

Synthesis of 4-hydroxyphenylphenylperylenylphosphine borane (5)

4-Hydroxyphenylphenylperylenylphosphine oxide (293 mg, 0.63 mmol) was dissolved in 20 mL of toluene, and triethylamine (900 μL, 6.26 mmol, 8 eq) was added dropwise to the solution. The mixture was stirred on ice. Trichlorosilane (780 μL, 7.8 mmol, 12 eq) was added dropwise to the mixture over 10 minutes, which was then refluxed at 110° C. After stirring for 18 hours, borane THF complex (1.23 mL, 1.2 mmol, 2 eq) was added dropwise to the mixture on ice. After stirring for 15 minutes, 10 mL of methanol was added to terminate the reaction. Yellow precipitates were removed by suction filtration and the filtrate was concentrated on an evaporator. Reddish brown crystals obtained were subjected to column chromatography using a developing solvent (dichloromethane) to give pale yellow crystals (yield 83%). The crystals obtained were identified by $^1$H-NMR, $^{31}$P-NMR, $^{13}$C-NMR, IR and UV.

$^1$H-NMR (CDCl$_3$, 400 MHz) δ 6.92 (d, J=3.6 Hz, 2H), 7.20-7.23 (m, 1H), 7.37 (t, J=8.2 Hz, 1H), 7.45-7.76 (m, 11H), 7.99-8.07 (m, 2H), 8.16-8.20 (m, 3H).

$^{31}$P-NMR (CDCl$_3$, 162 MHz) δ 20.12 (br).

$^{13}$C-NMR (CDCl$_3$, 100 Hz) δ 116.45, 116.56, 116.63, 119.15, 119.27, 119.76, 120.90, 121.09, 121.63, 125.05, 125.60, 126.79, 126.98, 127.12, 127.80, 127.87, 128.40, 129.10, 129.20, 129.33, 129.41, 129.48, 129.53, 130.11, 130.25, 130.95, 131.44, 131.93, 132.84, 132.94, 133.44, 133.54, 134.56, 134.93, 134.99, 135.09, 135.24, 135.35, 135.63, 135.74, 158.94. IR 810.14, 1100.33, 1170.57, 1253.73, 1498.76, 1595.37, 2927.87, 3050.72;

UV: 428 nm, 454 nm.

Synthesis of MitoPeDPPB (6)

In a globe box, 38.4 mg (1.1 eq, 0.58 mmol) of sodium hydride was washed 3 times with hexane (1 mL). After the residual hexane was dried using an oil pump, 2 mL of DMF was added to the sodium hydride followed by stirring at room temperature for 10 minutes. A DMF (2 mL) solution containing 245 mg (0.52 mmol) of 4-hydroxyphenylphenylperylenylphosphine borane was slowly added dropwise to the resulting solution mixture, followed by stirring at room temperature for 2.5 hours. The reaction solution gradually turned to a deep red turbid solution and at the same time, bubbles were generated. This reaction solution was cooled to −15° C. on an ice bath, and a DMF (1 mL) solution containing 290 mg (1 eq, 0.52 mmol) of iodopropylphosphonium iodide was slowly added dropwise to the reaction solution. The mixture was allowed to warm to room temperature and stirred overnight. It was confirmed by thin layer chromatography that the reaction preceded. Then 5 mL of saturated ammonium chloride aqueous solution was slowly added dropwise to the mixture. After extraction with dichloromethane, the extract was dried over sodium sulfate. The solvent was removed to give deep red oil. Purification was performed by silica gel column chromatography (dichloromethane:ethyl acetate=3:7) (yield 41%). The compound obtained was identified by $^1$H-NMR, $^{31}$P-NMR, IR, ESI-MS and elemental analysis.

$^1$H-NMR (CDCl$_3$, 400 MHz) δ 2.22 (m, 2H), 4.04 (m, 2H), 4.41 (m, 2H), 6.95 (d, J=3.4 Hz, 2H), 7.35 (t, J=4 Hz, 1H), 7.39-7.59 (m, 8H), 7.65-7.87 (m, 22H), 8.01 (d, J=4.2 Hz, 1H), 8.10 (d, J=3.8 Hz, 1H), 8.20 (d, J=3.6 Hz, 3H).

$^{13}$C-NMR (CDCl$_3$, 100 Hz) δ 20.24 d, J$_{cp}$=43.7 22.98, 67.01 (d, J$_{cp}$=8.4), 115.50, 115.62, 117.60, 118.46, 119.27, 119.38, 119.71, 120.34, 120.90, 121.11, 121.71, 124.98, 125.54, 126.86, 126.99, 127.13, 127.71, 127.79, 128.38, 128.44, 129.14, 129.24, 129.35, 129.48, 129.95, 130.22, 130.77, 130.90, 131.54, 131.96, 133.40, 133.50, 133.86, 133.97, 134.54, 134.96, 135.07, 135.24, 135.38, 135.49, 160.97.

$^{31}$P-NMR (CDCl$_3$, 162 MHz) δ 19.94 (br), 25.91.

IR 687.41, 737.06, 1105.67, 1253.35, 1435.94, 1498.13, 1590.88, 2380.33.

ESI-MS for C$_{53}$H$_{41}$O$_2$P$_2$: Calcd.: 755.26. Found: 755.29.

Elemental analysis (C$_{53}$H$_{44}$BIOP$_2$.2H$_2$O): Calcd.: C, 68.26; H, 5.19. Found: C, 68.21; H, 5.07.

Synthesis of MitoPeDPP (7)

MitoPeDPPB (60 mg, 0.067 mmol) was dissolved in 1 mL of chloroform, and diethylamine (52 μL, 0.52 mmol, 8 eq) was added dropwise to the solution. The mixture was stirred overnight at 40° C. on a water bath. The solvent was concentrated on an evaporator. The residue was purified by silica gel column chromatography using a developing solvent (dichloromethane:methanol=20:1). The solvent was concentrated to give reddish brown crystals (yield 62%). The compound was identified by $^1$H-NMR, $^{31}$P-NMR, $^{13}$C-NMR, IR, ESI-MS and UV.

$^1$H-NMR (CDCl$_3$, 400 MHz) δ 2.17 (m, 2H), 3.92-3.99 (m, 2H), 4.31 (m, 2H), 6.84 (d, J=4.2 Hz, 2H), 6.93-7.00 (m, 1H), 7.11-7.53 (m, 12H), 7.63-7.83 (m, 21H), 8.02 (d, J=3.8 Hz, 1H), 8.10 (d, J=3.8 Hz, 1H), 8.14-8.23 (m, 3H). $^{31}$P-NMR (CDCl$_3$, 162 MHz) δ −13.85, 25.78

$^{13}$C-NMR (CDCl$_3$, 100 Hz) δ 20.20 J$_{cp}$=26.3 Hz 23.08, 66.84, 115.31, 115.39, 117.74, 118.60, 120.72, 120.83, 126.08, 126.35, 126.87, 127.04, 128.20, 128.47, 128.65, 128.86, 128.93, 129.18, 130.71, 130.84, 131.06, 131.35, 131.86, 132.45, 132.80, 133.88, 133.98, 134.21, 134.77, 135.41, 136.15, 136.36, 136.68, 159.48

IR 686.99, 810.59, 1109.21, 1239.95, 1434.91, 1494.37, 1588.13, 3048.96.

ESI-MS (C$_{53}$H$_{41}$O$_2$P$_2$): Calcd.: 755.26. Found: 755.36.

UV: 433 nm, 463 nm

Synthesis of Iodopropanediphenylpyrenylphosphonium Iodide

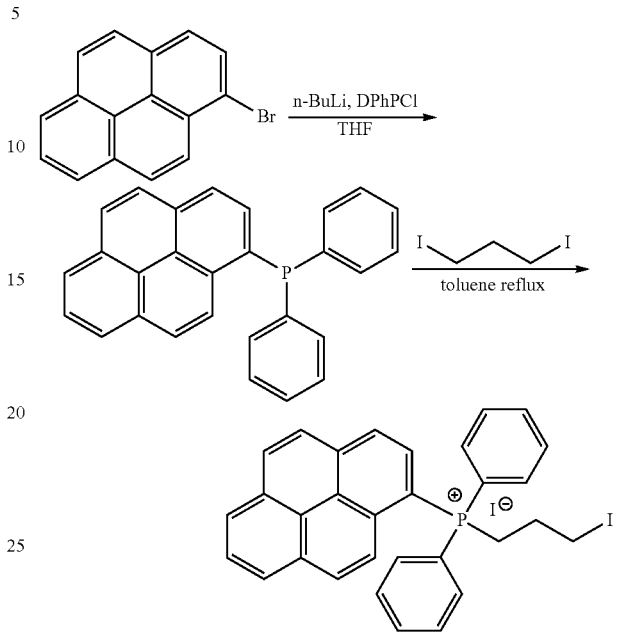

Bromopyrene (5 mmol, 1.41 g) was charged and dissolved in THF (25 ml). After the solution was cooled to −78° C., n-BuLi (5.5 mmol, 2.08 ml, 2.64 M, 1.1 eq) was slowly added dropwise to the solution and the mixture was stirred for 2 hours. Then, diphenylphosphine chloride (5 mmol, 0.92 ml, 1 eq) was slowly added dropwise to the mixture, followed by stirring overnight. Saturated NH$_4$Cl (10 mL) was added to the mixture. The THF layer was separated from the aqueous layer. The aqueous layer was extracted with dichloromethane (50 mL×3). The organic layer and the THF layer were combined. The resulting mixture was dried over sodium sulfate and concentrated on an evaporator. The residue was purified by silica gel column chromatography (developing solvent: dichloromethane:hexane=1:3). Thus, diphenylpyrenylphosphine (DPPP) was obtained (yield 39%) as white yellow crystals. The crystals were identified by $^1$H-NMR and $^{31}$P-NMR.

$^1$H-NMR (CDCl$_3$, 400 MHz) δ 7.33-7.37 (m, 10H), 7.53-7.56 (dd, J=7.8 Hz, 1H), 7.98-8.10 (m, 5H), 8.17-8.20 (m, 2H), 8.75-8.78 (dd, J=7.9 Hz, 1H)

$^{31}$P-NMR (CDCl$_3$, 162 MHz) δ −12.84

Diiodopropane (0.6 mmol, 175 mg) was dissolved in toluene (1 mL) and the solution was refluxed, during which a toluene (1 mL) solution containing dipyrenylphosphine (0.6 mmol, 232 mg, 1 eq) obtained was dropwise added thereto. After stirring overnight, the yellow precipitates formed were removed by suction filtration and washed 3 times with warm toluene. The crystals were dried to give iodopropanediphenylpyrenylphosphonium iodide (yield 63%). The product was identified by $^1$H-NMR, $^{31}$P-NMR, $^{13}$C-NMR, ESI-MS, IR and elemental analysis. m.p. 157-158° C.

$^1$H-NMR (CD$_3$OD, 400 MHz) δ 2.14-2.16 (m, 2H), 3.38-3.41 (t, J=3.2 Hz, 2H), 3.82-3.83 (m, 2H), 7.77-7.79 (m, 4H), 7.89-7.97 (m, 7H), 8.21-8.33 (m, 3H), 8.43-8.45 (d, J=7.6 MZ, 1H), 8.47-8.53 (m, 4H)

$^{31}$P-NMR (CD$_3$OD, 162 MHz) δ 24.06

$^{13}$C-NMR (DMSO-d$_6$, 100 MHz) δ 6.40-6.61, 24.79-25.30, 28.06, 108.40, 109.25, 119.44, 120.28, 123.51, 124.34, 126.12, 126.25, 127.81, 128.44, 128.79, 128.91, 130.02, 131.15, 131.28, 131.54, 132.48, 13367, 133.93, 134.12, 134.22, 135.70, 136.70

IR 481.80, 2878.23, 3039.23, 3398.25

ESI-MS (C$_{31}$H$_{25}$IP): Calcd.: 555.41. Found: 555.03

Elemental analysis (C$_{31}$H$_{25}$IP): Calcd.: C, 54.57; H, 3.69. Found: C, 54.50; H, 4.06.

Synthesis of [diphenyl-4-phenoxyphosphino]diphenylpyrenylphosphonium iodide (PyMitoTP)

First, diphenyl-4-methoxyphenylphosphine was synthesized as shown below.

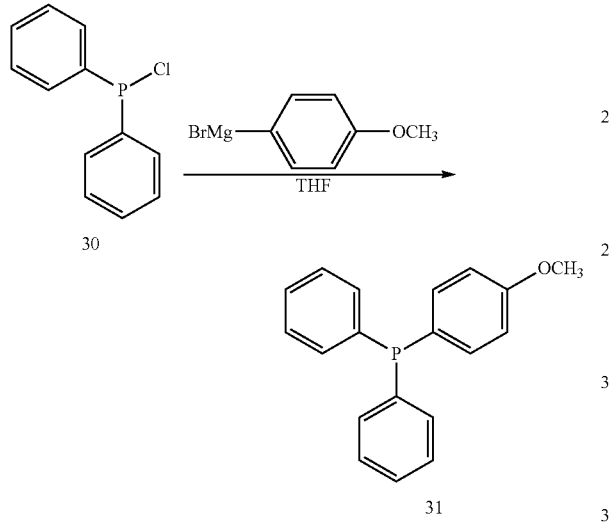

Diphenylphosphine chloride (5 mmol, 0.92 ml) was dissolved in TIM (25 ml). The solution was cooled to 0° C. 4-Methoxyphenyl magnesium bromide (6.5 mmol, 19 ml, 1.3 eq) was added dropwise to the solution over 20 minutes. The mixture was stirred for 3 hours. The mixture was allowed to warm to room temperature, and then stirred for another 5 hours after which saturated NH$_4$Cl (20 ml) was added thereto to terminate the reaction. The inorganic salt was removed by suction filtration and the filtrate was extracted with dichloromethane (40 ml×3). The extract was dried over sodium sulfate and concentrated using an evaporator and an oil pump to give diphenyl-4-methoxyphenylphosphine.

Next, diphenyl-4-methoxyphenylphosphine obtained was treated in the same manner as the synthesis of MitoDPPP to give the phosphine borane described below (yield 20%).

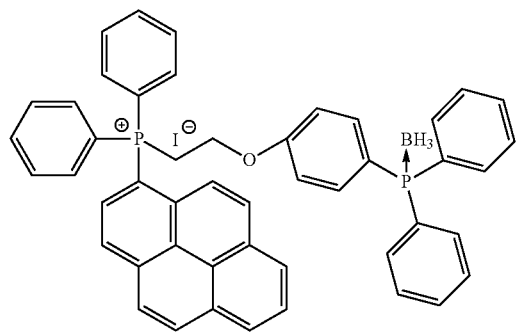

$^1$H-NMR (CDCl$_3$, 400 MHz) δ 2.23-2.24 (d, J=5.2, 2H), 4.29-4.30 (dd, 3.6, 2H), 4.40-4.42 (m, 2H), 6.88-6.90 (d, J=8.8, 2H), 7.39-7.55 (m, 12H), 7.65-7.70 (m, 4H), 7.77-7.80 (m, 2H), 7.93-7.98 (m, 5H), 8.15-8.23 (m, 3H), 8.34-8.43 (m, 5H)

$^{31}$P-NMR (CDCl$_3$, 162 MHz) δ 19.98, 25.68.

ESI-MS (C$_{49}$H$_{42}$BIOP$_2$): Calcd.: 706.52. Found: 706.15.

From the phosphine borane obtained above, [diphenyl-4-phenoxyphosphino]diphenylpyrenylphosphonium iodide (PyMitoTP) was synthesized by the procedure as follows:

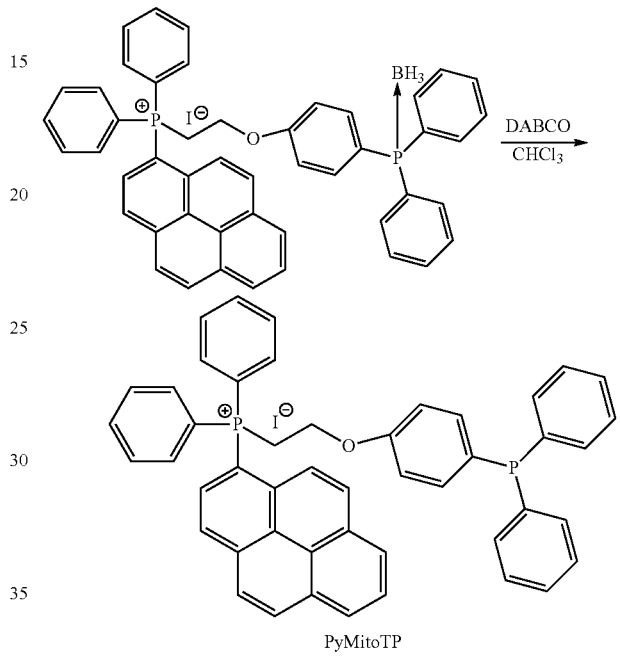

PyMitoTP

The phosphine borane (20 mg, 0.02 mmol) was dissolved in CHCl$_3$ (2 ml), and a CHCl$_3$ (1 ml) solution of DABCO (2 mg, 0.02 mmol, 1 eq) was dropwise added thereto. The mixture was stirred at 40° C. overnight. The solvent was concentrated using an evaporator and an oil pump. The residue was purified by column chromatography (developing solvent: dichloromethane:methanol=40:1) (yield 10%). The product was identified by $^1$H-NMR and $^{31}$P-NMR.

$^1$H-NMR (CDCl$_3$, 400 MHz) δ 2.22 (s, 2H), 4.28-4.29 (d, J=3.6, 2H), 4.32-4.33 (d, J=5.2, 2H), 6.80-6.82 (d, J=8.4, 2H), 7.18-7.23 (t, J=10, 2H), 7.30-7.60 (m, 10H), 7.67-7.70 (m, 4H), 7.76-7.78 (m, 2H), 7.94-7.99 (m, 5H), 8.15-8.23 (m, 3H), 8.34-8.43 (m, 5H)

$^{31}$P-NMR (CDCl$_3$, 162 MHz) δ -5.96, 25.71.

Example 4

The time scale changes in fluorescence intensity were monitored for the oxidation with hydrogen peroxide of [3-(4-Phenoxyphenylphosphinopyrenylphosphino)propyl]triphenylphosphonium iodide [Ia] (MitoDPPP) obtained in EXAMPLE 1.

After 10 mM H$_2$O$_2$ was added dropwise to a dimethylsulfoxide solution of MitoDPPP (16 μM), fluorescence intensities at the fluorescence wavelength of 380 nm were measured for 10 minutes. The results are shown in FIG. 1. As shown in FIG. 1, it is observed that gradual oxidation of MitoDPPP resulted in an increase in the fluorescence intensity.

The reaction scheme of the oxidation of MitoDPPP [Ia] to MitoDPPP [XIa] is as follows:

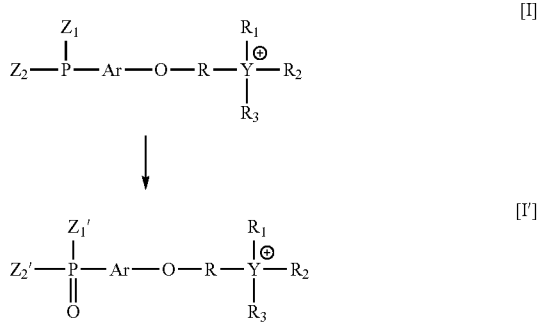

Example 5

Figure 2:
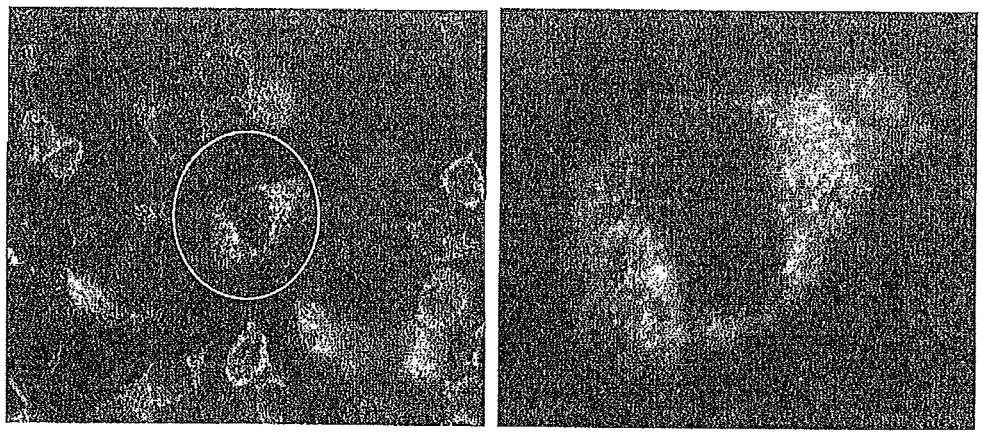
FIG. 2 shows the loading of MitoDPPP into HepG2 cells (EXAMPLE 5).
Figure 2:
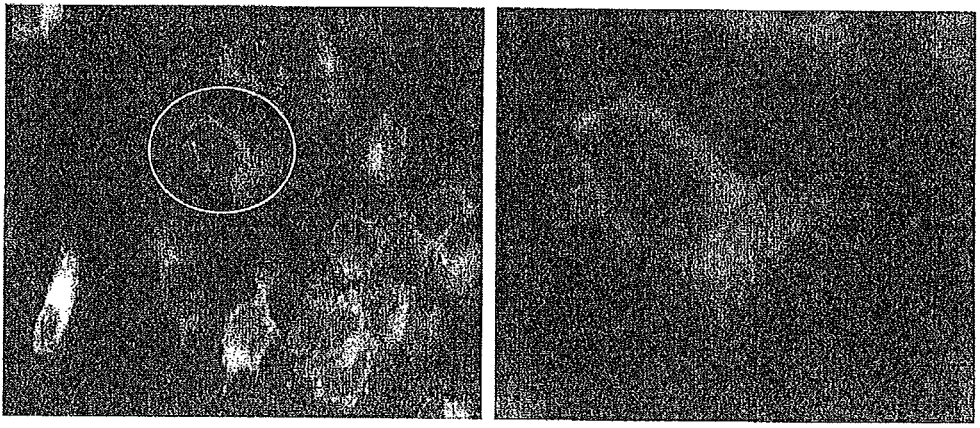

Loading of MitoDPPP into HepG2 cells was examined. A 20% dimethylsulfoxide solution of MitoDPPP (16 μM) was prepared and the solution was loaded into HepG2 cells for 10 minutes to stain the cells. After washing with PBS, the cells were observed under a fluorescence microscope. The results are shown in FIG. 2. As a result of comparison in staining with mitochondria-selective fluorescent dye Mito Tracker Green FM, it was revealed that MitoDPPP was localized in mitochondria, as shown in FIG. 2. FIG. 2(a) shows the results of staining with mitochondria-selective fluorescent dye Mito Tracker Green FM, in which the right panel is an enlarged image of the circle shown in the left panel. FIG. 2(b) shows the results of staining with MitoDPPP, in which the right panel is an enlarged image of the circle shown in the left panel.

Example 6

Figure 3:
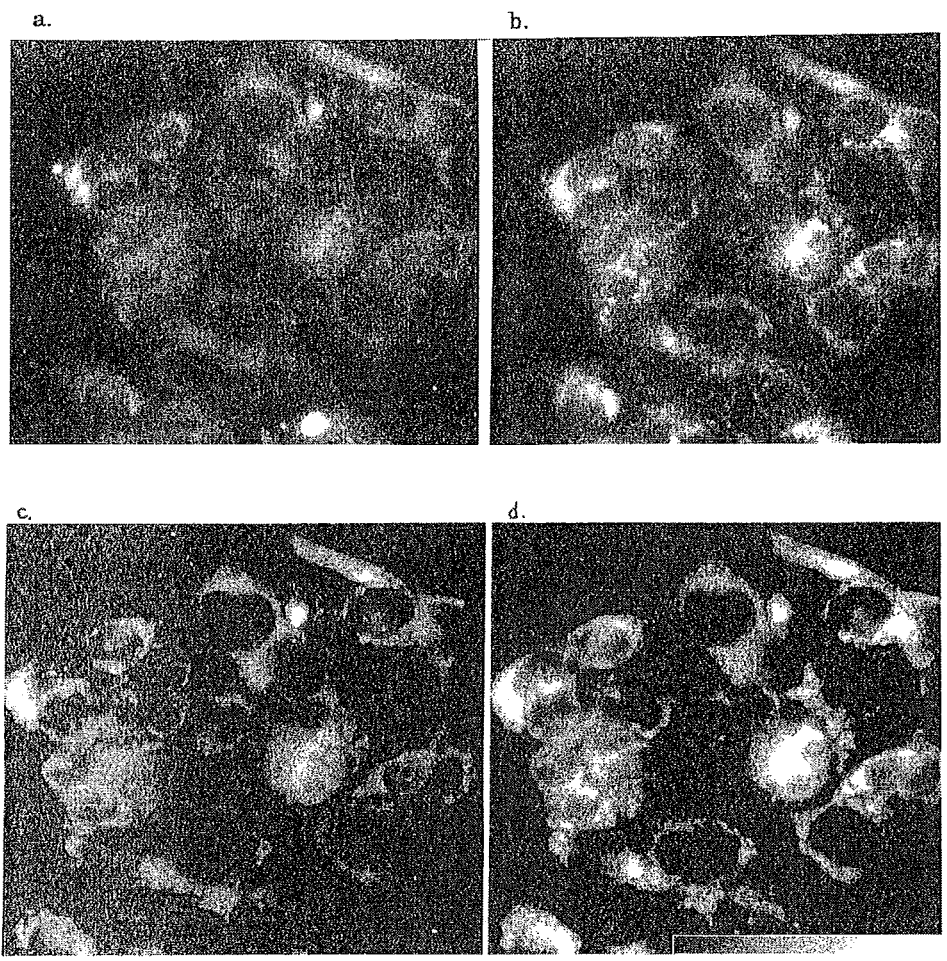
FIG. 3 shows the loading of MitoDPPP into HepG2 cells and the oxidation by stimulation with tert-butoxyhydroperoxide (tBHP) (EXAMPLE 6).

Loading of MitoDPPP into HepG2 cells and oxidation stimulated with tert-butoxyhydroperoxide (tBHP) were monitored. A 0.1% dimethylsulfoxide solution of MitoDPPP (16 μM) was prepared. The solution was loaded into HepG2 cells for 2 minutes to stain the cells. The cells were washed with PBS and observed under a fluorescence microscope. Next, tert-butoxyhydroperoxide (tBHP) was added to the cells. Ten minutes later, the cells were observed under the fluorescence microscope. The results are shown in FIG. 3. In the figure, panel (a) shows the MitoDPPP stained cells before tBHP loading, panel (b) shows the MitoDPPP stained cells after tBHP loading, panel (c) shows brightness distribution of (a), and (d) indicates brightness distribution (b). These results reveal that brightness of (b) was increased compared to that of (a), as a result of the oxidation of MitoDPPP localized in the mitochondria with tBHP.

Example 7

Figure 4:
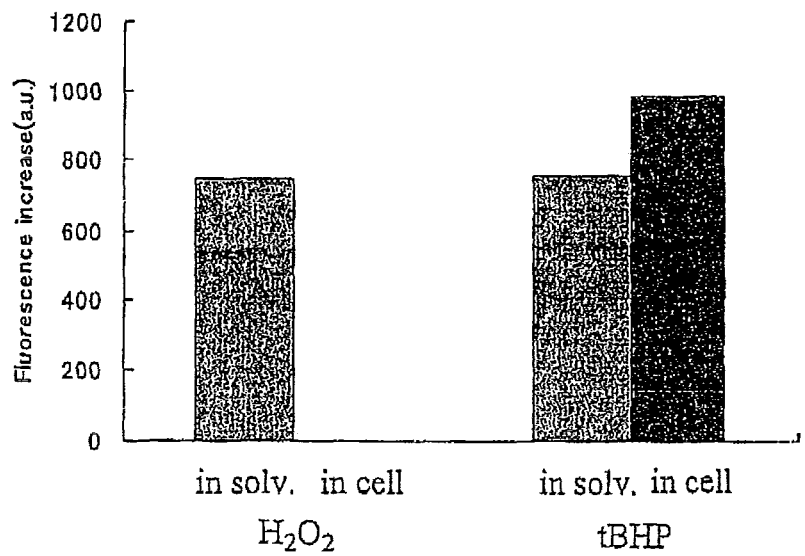
FIG. 4 shows the results of comparison in the oxidation of MitoDPPP loaded into HepG2 cells with hydrogen peroxide and tBHP (EXAMPLE 7).

The oxidation of MitoDPPP loaded into HepG2 cells was compared for hydrogen peroxide and tBHP. A 0.1% dimethylsulfoxide solution of MitoDPPP (16 μM) was prepared. The solution was loaded into HepG2 cells for 10 minutes. After washing the cells with PBS, hydrogen peroxide was added to the cells and the increase in fluorescence intensity was monitored on a microplate reader. The results are shown in FIG. 4. As a result, it is revealed that the oxidation of MitoDPPP in an aqueous solution proceeds rapidly with both hydrogen peroxide and tBHP, whereas MitoDPPP loaded into HepG2 cells is not oxidized with hydrogen peroxide.

Example 8

A 1% DMSO-containing Dulbecco's phosphate buffer solution supplemented with MitoDPPP (1.6 μM), ascorbic acid, an ascorbic acid derivative (25 μM) and AAPH (25 μM) was prepared. The solution was warmed to 37° C. and changes in fluorescence intensity were monitored using a fluorescence spectrophotometer.

Figure 5:
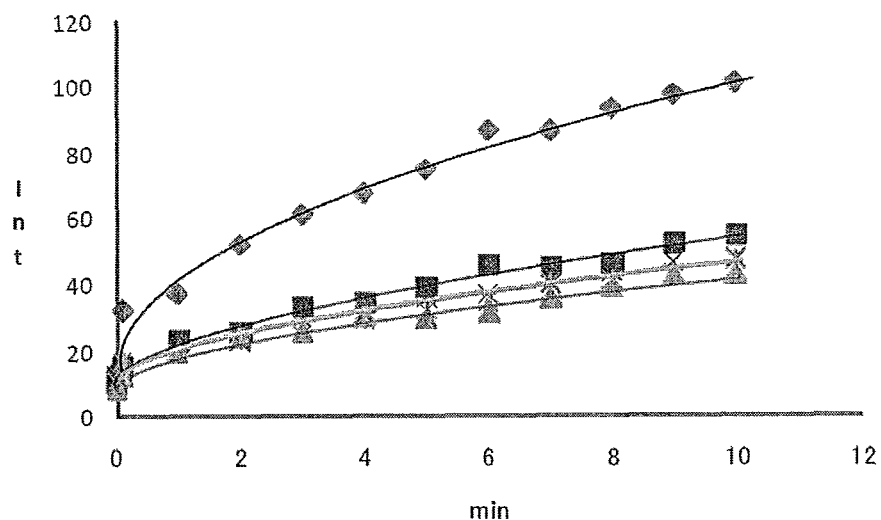
FIG. 5 shows time scale changes in fluorescence intensity of MitoDPPP in an aqueous solution (EXAMPLE 9).
Figure 6:
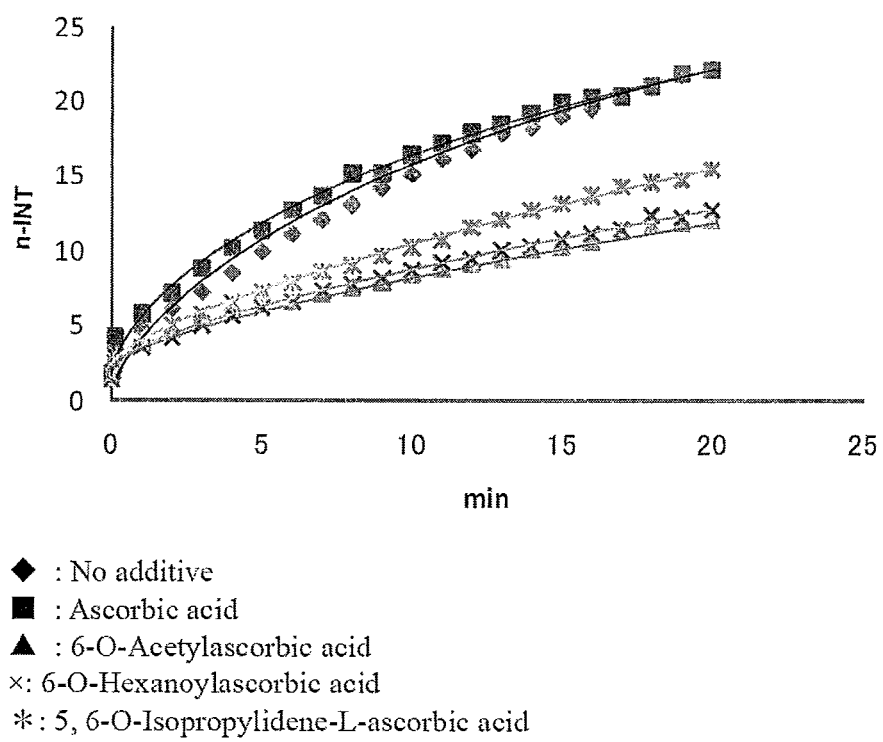
FIG. 6 shows time scale changes in fluorescence intensity resulting from the oxidation of MitoDPPP in cells in the presence of ascorbic acid (EXAMPLE 9).

Next, a glass plate with HepG2 cells cultured on its surface was fixed diagonally at the center of a quartz cell, and 3 mL of DPBS was added to the cells. Auto-fluorescence was measured (excitation wavelength: 281 nm, fluorescence wavelength: around 340 nm), and then the plate was placed in a Petri dish and washed twice with 1 mL of PBS. Then, 2 mL of MitoDPPP (16 μM) solution was charged in the Petri dish, followed by incubation at 37° C. for 20 minutes. The solution was removed and the cells were washed twice with 1 mL of DPBS. Next, 2 mL of an ascorbic acid (25 μM) solution, a 6-O-acetylascorbic acid (25 μM) solution, a 6-O-hexanoylascorbic acid (25 μM) solution and a 5, 6-O-isopropylidene-L-ascorbic acid (25 μM) solution were prepared, respectively. Each solution was charged in a Petri dish and incubated at 37° C. for 30 minutes. After loading, the solution was removed and the cells were washed twice with 1 mL of PBS. DPBS (1980 μL) was warmed to 37° C. and charged in the quartz cell. A magnet was used to hold the plate at the center of the quartz cell, and the fluorescence intensity (excitation wavelength: 353 nm, fluorescence wavelength: 380 nm) was measured. After 20 μL (final concentration, 250 μM) of the solution of AAPH (25 μM) in 1 mL of DPBS, which had been previously cooled, was added to the cells and warmed to 37° C., an increase in the fluorescence intensity was monitored using a fluorescence spectrophotometer. The results are shown in FIG. 5 and FIG. 6.

Example 9

Comparison in Antioxidant Potential of Antioxidants in Cells

First, MitoDPPP is oxidized using a radical initiator AAPH. When ascorbic acid and its derivatives are added during the oxidation, the increase in fluorescence intensity is suppressed. The extent of this suppression corresponds to the antioxidant potential of ascorbic acid and its derivatives. FIG. 5 shows time scale changes in fluorescence intensity in an aqueous solution.

Next, the antioxidant activities of ascorbic acid and a preliminarily synthesized lipophilic derivative thereof in HepG2 cells were compared. HepG2 cells were incubated on a glass plate and the auto-fluorescence inherent to the cells on the plate was measured. Then, MitoDPPP and the ascorbic acid derivative were loaded into the cells and subsequently, AAPH was loaded into the cells, whereby the reaction was initiated. By dividing the fluorescence intensity measured by the auto-fluorescence, the increase in fluorescence intensity was normalized. FIG. 6 shows time scale changes in fluorescence intensity resulting from the oxidation of MitoDPPP in the cells in the presence of ascorbic acid.

INDUSTRIAL APPLICABILITY

The phosphine compounds in accordance with this invention can scavenge peroxides localized in mitochondria which are particularly vulnerable to oxidative stress. Since the degree of oxidative stress, which causes damages against the function of mitochondrial membrane to induce apoptosis, can be visualized using fluorescence probes, the phosphine compounds are useful as peroxide scavengers in mitochondria.

The invention claimed is:

1. A phosphine compound represented by general formula [I]:

$$Z_2-\underset{\underset{}{|}}{\overset{\overset{Z_1}{|}}{P}}-Ar-O-R-\underset{\underset{R_3}{|}}{\overset{\overset{R_1}{|}\oplus}{Q}}-R_2 \quad X^{\ominus} \qquad [I]$$

wherein:
$Z_1$ and $Z_2$ each represents a cyclic group,
Ar represents an arylene group,
R represents an aliphatic hydrocarbon group,
Q represents phosphorus (P), nitrogen (N) or bismuth (Bi), and,
$R_1$, $R_2$ and $R_3$ each represents a cyclic group, and
X represents a halogen atom.

2. The phosphine compound according to claim 1, wherein:
the cyclic groups represented by $Z_1$ and $Z_2$ both are unsubstituted or substituted, monocyclic hydrocarbon groups or polycyclic hydrocarbon groups or hetero-monocyclic groups or hetero-polycyclic groups;
the arylene group represented by Ar is an unsubstituted or substituted monocyclic hydrocarbon group or bicyclic hydrocarbon group;
the aliphatic hydrocarbon group represented by R is a linear or branched bivalent aliphatic hydrocarbon group having 1 to 8 carbon atoms;
the cyclic groups represented by $R_1$, $R_2$ and $R_3$, which may be the same or different, each represents a cationic group shown by which represents an unsubstituted or substituted monocyclic hydrocarbon group or polycyclic hydrocarbon group or hetero-monocyclic group or hetero-polycyclic group;
with the proviso that either one of the cyclic groups represented by $Z_1$ and $Z_2$ is a monocyclic hydrocarbon group or a hetero-monocyclic group and the other cyclic group is a polycyclic hydrocarbon group or a hetero-polycyclic group, and/or either one of the cyclic groups represented by $R_1$, $R_2$ and $R_3$ is a monocyclic hydrocarbon group or a hetero-monocyclic group, and the other cyclic group(s) is/are a polycyclic hydrocarbon group(s) or a hetero-polycyclic group(s).

3. The phosphine compound according to claim 2, wherein either one of the cyclic groups represented by $Z_1$ and $Z_2$ is a polycyclic hydrocarbon group or a hetero-polycyclic group, the other monocyclic group is a monocyclic hydrocarbon group or a hetero-monocyclic group, all of the cyclic groups represented by $R_1$, $R_2$ and $R_3$ are monocyclic hydrocarbon groups or hetero-monocyclic groups, or, the monocyclic groups in all of the cyclic groups represented by $Z_1$ and $Z_2$ are monocyclic hydrocarbon groups or hetero-monocyclic groups, either one of the cyclic groups represented by $R_1$, $R_2$ and $R_3$ is a polycyclic hydrocarbon group or a hetero-polycyclic group, and the other cyclic group(s) is/are a monocyclic hydrocarbon group(s) or a hetero-monocyclic group(s).

4. The phosphine compound according to claim 2 or 3, wherein:
the cyclic groups represented by $Z_1$, $Z_2$, $R_1$, $R_2$ and $R_3$ each represents
a monocyclic hydrocarbon group;
a bicyclic hydrocarbon group;
a tricyclic hydrocarbon group;
a tetracyclic hydrocarbon group;
a pentacyclic hydrocarbon group;
a hexacyclic hydrocarbon group
a heptacyclic hydrocarbon group;
the heterocyclic group is a hetero-monocyclic group comprising a N-containing hetero-monocyclic group, an O-containing hetero-monocyclic group, a S-containing hetero-polycyclic group, and a N/O/S-containing hetero-monocyclic group;
a hetero-polycyclic group including a N-containing hetero-polycyclic group comprising a N-containing hetero-bicyclic group, and a N-containing hetero-tricyclic group, an O-containing hetero-polycyclic group comprising an O-containing hetero-bicyclic group, and an O-containing hetero-tricyclic group;
a S-containing hetero-polycyclic group comprising a S-containing hetero-tricyclic group, a S-containing hetero-tricyclic group;
and a N/O/S-containing hetero-polycyclic group, wherein the substituent is a lower aliphatic hydrocarbon group having 1 to 6 carbon atoms;
the arylene group represented by Ar is phenylene or naphthalene; and
the linear or branched bivalent aliphatic hydrocarbon group represented by R is methylene, ethylene, propylene, isopropylene, butylene or methylbutylene.

5. A process for producing a phosphine compound, which comprises yielding a phosphine compound [I]:

$$Z_2-\underset{\underset{}{|}}{\overset{\overset{Z_1}{|}}{P}}-Ar-O-R-\underset{\underset{R_3}{|}}{\overset{\overset{R_1}{|}\oplus}{Q}}-R_2 \quad X^{\ominus} \qquad [I]$$

or a phosphine compound [XVIII]:

$$Z_2-\underset{\underset{}{|}}{\overset{\overset{Z_1}{|}}{P}}-Ar-O-R-\underset{\underset{R_3}{|}}{\overset{\overset{R_1}{|}\oplus}{Q}}-R_2 \quad Xg^{\ominus} \qquad [XVIII]$$

by:
a process comprising Step 1a: reacting a halide compound represented by formula [II]:

$$Z_1-X_1 \qquad [II]$$

a dihalophosphine compound [III]:

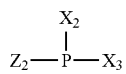

[III]

and a methoxyaryl-metal magnesium halide [IV]:

[IV]

to obtain a methoxyarylphosphine compound [V]:

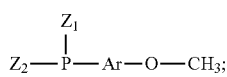

[V]

Step 2: reacting the methoxyarylphosphine compound [V] obtained in Step 1a above with an oxidizing agent to obtain a methoxyarylphosphine oxide compound [VI]:

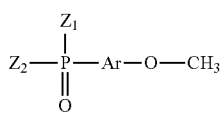

[VI]

Step 3: demethylating the methoxyarylphosphine oxide compound [VI] obtained in Step 2 above with a demethylating reagent to obtain a hydroxyarylphosphine oxide compound [VII]:

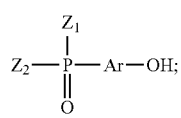

[VII]

Step 4: reacting the hydroxyarylphosphine oxide compound [VII] obtained in Step 3 above with a borane compound to obtain a hydroxyarylphosphine borane compound [VIII]:

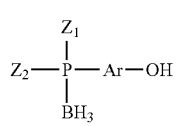

[VIII]

Step 5: reacting the dicyclic group-substituted hydroxymethoxyarylphosphine borane compound [VII] obtained in Step 4 above with a halide compound [IX]:

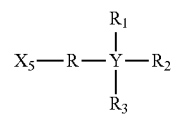

[IX]

to obtain a phosphine borane compound represented by general formula [X]:

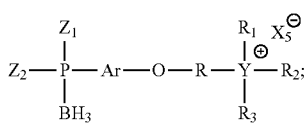

[X]

and

Step 6: removing the protecting group from the phosphine borane compound [X] obtained in Step 5 above to yield a phosphine compound represented by general formula [I]; or, a process comprising Step 1b: reacting the halide compound [II] with a methoxyarylphosphine oxide compound [XI]:

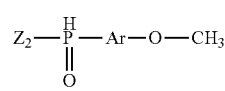

[XI]

to obtain the dicyclic group-substituted methoxyarylphosphine oxide compound [VI];

Step 3: demethylating the methoxyarylphosphine oxide compound [VI] obtained in Step 1b with a demethylating reagent to obtain the hydroxyarylphosphine oxide compound [VII];

Step 4: reacting the hydroxyarylphosphine oxide compound [VII] obtained in Step 3 with a borane compound to obtain the hydroxyarylphosphine borane compound [VIII];

Step 5: reacting the hydroxyarylphosphine borane compound [VIII] obtained in Step 4 with the halide compound [IX] to obtain a phosphine borane compound [X]; and Step 6: removing the protecting group from the phosphine borane compound [X] obtained in Step 5 to yield a phosphine compound represented by general formula [I]; or, a process comprising Step 7: reacting a halide compound [XII]:

[XII]

with a halide compound [XIII]:

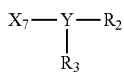

[XIII]

to obtain a compound [XIV]:

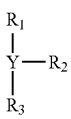

[XIV]

Step 8: reacting the compound [XIV] obtained in Step 7 above with a dihalo-compound [XV]:

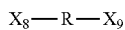

[XV]

to obtain a halo-compound [XVI]:

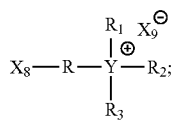

[XVI]

Step 9: reacting the halo-compound [XVI] obtained in Step 8 above and the hydroxyarylphosphine borane compound [VIII] obtained in Step 4 above with a substituted alkyl halide [XVI] to obtain a phosphine borane compound [XVII]:

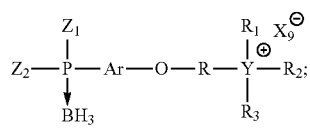

[XVII]

and

Step 10: deprotecting the phosphine borane compound [VI] obtained in Step 9 above to yield a phosphine compound [XVIII] or [I], wherein in formulas [I] to [XVIII]:

$Z_1$ and $Z_2$ each represents a cyclic group,

Ar represents an arylene group,

R represents an aliphatic hydrocarbon group,

Y represents phosphorus (P), nitrogen (N) or bismuth (Bi), $R_1$, $R_2$, $R_3$ each represents a cyclic group, X represents a halogen atom, and each of $X_1$ to $X_9$, which may be same or different, represents a halogen atom, and Q represents phosphorous (P), nitrogen (N) or bismuth (Bi).

6. A peroxide scavenger comprising the phosphine compound represented by general formula m as recited in claim 1.

7. A method for scavenging a peroxide which comprises:
reacting the phosphine compound represented by general formula [I] recited in claim 1 with a peroxide; and
detecting an increase in fluorescence intensity of the phosphine compound represented by general formula [I].

8. The method for scavenging a peroxide according to claim 7, wherein the peroxide is a reactive oxygen species including a lipid peroxide and singlet oxygen.

9. A phosphinyl compound represented by general formula [I']:

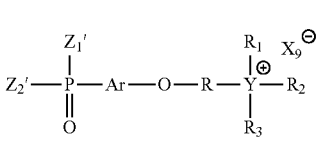

[I']

wherein $X_9$ is a halogen atom;

wherein each of $Z_1'$ and $Z_2'$ represents a cyclic group, wherein the cyclic groups represented by $Z_1'$ and $Z_2'$, which may be the same or different, are unsubstituted or substituted, monocyclic hydrocarbon groups or polycyclic hydrocarbon groups or hetero-monocyclic groups or hetero-polycyclic groups;

wherein each of $R_1$, $R_2$ and $R_3$, represents a cyclic group, which may be the same or different, a cationic group which represents an unsubstituted or substituted monocyclic hydrocarbon group or polycyclic hydrocarbon group or hetero-monocyclic group or hetero-polycyclic group;

with the proviso that when all of $R_1$, $R_2$ and $R_3$ represent monocyclic hydrocarbon groups, either one of them is a cyclic group other than monocyclic hydrocarbon group, or when $Z_1'$ and $Z_2'$ both represent monocyclic hydrocarbon groups, one of $R_1$, $R_2$ and $R_3$ is a cyclic group other than monocyclic hydrocarbon group.

10. The phosphine compound according to claim 4, wherein:

the monocyclic hydrocarbon group is phenyl;

the bicyclic hydrocarbon group is indanyl, indenyl, pentalenyl, azulenyl, naphthyl or tetrahydronaphthyl;

the tricyclic hydrocarbon group is anthracenyl, fluorenyl, phenalenyl or phenanthrenyl;

the tetracyclic hydrocarbon group is pyrenyl, naphthacenyl or chrysenyl;

the pentacyclic hydrocarbon group is perylenyl, picenyl or pentacenyl;

the hexacyclic hydrocarbon group is naphthobyrenyl;

the heptacyclic hydrocarbon group is coronenyl;

the heterocyclic group is a hetero-monocyclic group including a N-containing hetero-monocyclic group is selected from the group consisting of pyrrolyl, imidazolyl, pyrazolyl, pyridyl, piperidyl and triazinyl;

the O-containing hetero-monocyclic group is furanyl or pyranyl;

the S-containing hetero-polycyclic group is thiophenyl;

the N/O/S-containing hetero-monocyclic group is oxazolyl, thiazolyl or morpholinyl;

the hetero-polycyclic group including a N-containing hetero-polycyclic group comprising the N-containing hetero-bicyclic group is indolyl, indolinyl, quinolinyl, isoquinolinyl, quinazolinyl, quinoxalinyl, naphthyridinyl, puteridinyl or purinyl;

the N-containing hetero-tricyclic group is acridinyl, carbazolyl, phenanthridinyl, phenazinyl or benzoisoquinolinyl;

the O-containing hetero-polycyclic group comprising the O-containing hetero-bicyclic group is benzofuranyl, chromanyl, chromenyl or isochromanyl;

the O-containing hetero-tricyclic group is xanthenyl;

the S-containing hetero-polycyclic group comprising the S-containing hetero-tricyclic group is dithianaphthyl;

the S-containing hetero-tricyclic group is thianthrenyl;

the N/O/S-containing hetero-polycyclic group is pyridoxazolyl, thienofuranyl, phenoxazinyl, phenothiazinyl or pyrazoloxazolyl, wherein the substituent is a lower aliphatic hydrocarbon group having 1 to 6 carbon atoms selected from the group consisting of methyl, ethyl, propyl or isopropyl;

the arylene group represented by Ar is phenylene or naphthalene; and the linear or branched bivalent aliphatic hydrocarbon group represented by R is methylene, ethylene, propylene, isopropylene, butylene or methylbutylene.

11. The method for scavenging a peroxide comprising:
(a) loading cells with the phosphine compound according to claim 1; and
(b) visualizing the state of oxidative stress in mitochondria of the cells.

* * * * *